(12) United States Patent
Ursin et al.

(10) Patent No.: US 8,329,994 B2
(45) Date of Patent: Dec. 11, 2012

(54) **UTILIZATION OF FATTY ACID DESATURASES FROM *HEMISELMIS SPP***

(75) Inventors: Virginia Ursin, Pawcatuck, CT (US); Byron Froman, Davis, CA (US); Steven Screen, St. Louis, MO (US); Lori Lehman, Vacaville, CA (US)

(73) Assignee: Monsanto Technology LLC, St. Louis, MO (US)

( * ) Notice: Subject to any disclaimer, the term of this patent is extended or adjusted under 35 U.S.C. 154(b) by 361 days.

(21) Appl. No.: 12/578,880

(22) Filed: Oct. 14, 2009

(65) Prior Publication Data
US 2010/0092640 A1    Apr. 15, 2010

Related U.S. Application Data

(60) Provisional application No. 61/105,316, filed on Oct. 14, 2008.

(51) Int. Cl.
*A01H 5/00* (2006.01)
*C12N 15/82* (2006.01)
*C12N 1/20* (2006.01)
*C07H 21/04* (2006.01)
*A61K 36/00* (2006.01)

(52) U.S. Cl. ....... 800/298; 800/281; 536/23.2; 435/419; 435/252.3; 424/725

(58) Field of Classification Search .................. None
See application file for complete search history.

(56) References Cited

U.S. PATENT DOCUMENTS

| | | | |
|---|---|---|---|
| 6,459,018 B1 | 10/2002 | Knutzon | 800/320.3 |
| 7,037,692 B1 | 5/2006 | Thompson et al. | |
| 7,622,632 B2 | 11/2009 | Ursin et al. | 800/281 |
| 7,695,950 B2 | 4/2010 | Damude et al. | 435/254.11 |
| 7,705,215 B1 | 4/2010 | Adams et al. | |
| 2006/0156435 A1 | 7/2006 | Ursin et al. | |
| 2007/0249026 A1 | 10/2007 | Xue et al. | 435/134 |
| 2007/0271632 A1 | 11/2007 | Damude et al. | 435/254.11 |
| 2008/0020122 A1 | 1/2008 | Ursin et al. | |
| 2008/0063691 A1 | 3/2008 | Ursin et al. | |
| 2008/0260929 A1 | 10/2008 | Ursin et al. | |
| 2010/0212045 A1 | 8/2010 | Ursin et al. | |

FOREIGN PATENT DOCUMENTS

| | | |
|---|---|---|
| DE | 10 2006 008 030 | 8/2007 |
| EP | 0 978 563 | 2/2000 |
| WO | WO 2005/103253 | 11/2005 |
| WO | WO 2008/009600 | 1/2008 |
| WO | WO 2008/011468 | 1/2008 |

OTHER PUBLICATIONS

Domergue et al., "In vivo characterization of the first acyl-CoA delta[6]-desaturase from a member of the plant kingdom, the microalga *Ostreococcus tauri*," *Biochem J.*, 389:483-490, 2005.
GenBank Accession No. AAC72755, dated Nov. 11, 1998.
GenBank Accession No. AAF08685, dated Nov. 18, 1999.
GenBank Accession No. AAL13311, dated Mar. 24, 2005.
GenBank Accession No. DJ418329, dated May 23, 2008.
International Search Report for PCT Application No. PCT/US2009/060638, dated Jan. 27, 2010.
Singh et al., "Metabolic engineering of new fatty acids in plants," *Curr. Opin. Plant Biol.*, 8:197-203, 2005.
Zhou et al., "Isolation and characterization of genes from the marine microalga *Pavlova salina* encoding three front-end desaturases involved in docosahexaenoic acid biosynthesis," *Phytochemistry*, 68:785-796, 2007.

*Primary Examiner* — Elizabeth McElwain
(74) *Attorney, Agent, or Firm* — SNR Denton US LLP; Byron V. Olsen Esq.

(57) ABSTRACT

The invention relates to methods and compositions concerning desaturase enzymes that modulate the number and location of double bonds in long chain poly-unsaturated fatty acids (LC-PUFA's). In particular, the invention relates to methods and compositions for improving omega-3 fatty acid profiles in plant products and parts using exogenous desaturase enzymes and nucleic acids encoding for such enzymes. In particular embodiments, the exogenous desaturase enzymes utilized are *Hemiselmis* spp. delta 5 desaturases. Also provided are improved soybean oil compositions having EPA derived from plants carrying the genes of interest.

24 Claims, 6 Drawing Sheets

SEQUENCE LISTING

```
<160> NUMBER OF SEQ ID NOS: 25

<210> SEQ ID NO 1
<211> LENGTH: 1326
<212> TYPE: DNA
<213> ORGANISM: Hemiselmis virescens

<400> SEQUENCE: 1
atgcctccca acagtggcgc gggaggcgct gcctccgacc tcgaggtctt cccctccgcc      60
gatgaccttc ccgaggggta catcgccatc gatggggagg tctacgacct caaggggttc     120
gaccaccccg gagggaatc catcaatctc ttcgggggca acgacgtttc ggtgcagtat      180
cggatgatcc atcccttcca tcagggcaag ggggccgtca acaagatgaa gaaggtgggc     240
aggctcgcca gctctcgcct cgactacaag tttggcagcg acttcgagaa ggatgttatc     300
gccgccgtcg ccaaggttgt caaacccagc gagcgctttg cgacgcccgg attctggttc     360
cgctgcggtg cttacgtcac tgcttacgcg gggcttacct acgtgtacgt caccaagggc     420
tccagcctgc ccctctgcat tgccattggc atgtctcagg cctcaatcgg cctaaacgtg     480
cagcacgatg cgaatcacgg cgctgtgtcc gcttccccgt tctggaacga cctcctgggc     540
ttcggggcgg acatgattgg gggatgcaag tacctttggc ttcagcagca ctggacgcac     600
cacgccttta caaacgacat tacccgtgac cccgacgcct cgagcacgga ccccttcttc     660
ctcttccacg actatggcaa ggagactccc gtccgcaagg ccttccacat gtttcagcac     720
ttctacatgg tgcccgtgct cgcgatgtac tgggcatcct cgatcttcaa caccaatgtc     780
gttacgctgc agcacgcggg cgcggcggag gggggatga agttcgccaa ctcgtaccgt     840
gaggcgcacc gccccatctc gatcgccctc cgctcactct acctcggact ctactgcgcg     900 accccttct gctggcacag ctggcccacg gccctctctc atgtgtggac gatggctgtg     960
tcggagagcc tcacccttgc catccccttt gcgctttccc acaactttat ggagagcgag    1020
aggcacccgg tggcaaacgg gcaggcctgc tggtacaagg cgcaggtcga cgtcttccg    1080 acgtatgggg ggtacatcgc tgggtggctc acgggggggcc tcaactacca gattgagcac    1140
cacctgttcc ccaggatgtc atcggcttgg taccctaca tccagcccgc ggtgcgcgag     1200
gtctgcaaga agcacggcgt aaactacgtc tattacccaa acatatttgc caacctcgcc    1260
tccacgttcc agtacattgc gcaggtgggc caggggatct atgagaggag ggtcaaggcg    1320
gcctga                                                                1326

<210> SEQ ID NO 2
<211> LENGTH: 441
<212> TYPE: PRT
<213> ORGANISM: Hemiselmis virescens
```

```
<400> SEQUENCE: 2

Met Pro Pro Asn Ser Gly Ala Gly Gly Ala Ser Asp Leu Glu Val
1               5                   10                  15

Phe Pro Ser Ala Asp Asp Leu Pro Glu Gly Tyr Ile Ala Ile Asp Gly
            20                  25                  30

Glu Val Tyr Asp Leu Lys Gly Phe Asp His Pro Gly Gly Glu Ser Ile
                35                  40                  45

Asn Leu Phe Gly Gly Asn Asp Val Ser Val Gln Tyr Arg Met Ile His
50                  55                  60

Pro Phe His Gln Gly Lys Gly Ala Val Asn Lys Met Lys Lys Val Gly
65                  70                  75                  80

Arg Leu Ala Ser Ser Arg Leu Asp Tyr Lys Phe Gly Ser Asp Phe Glu
                85                  90                  95

Lys Asp Val Ile Ala Ala Val Ala Lys Val Val Lys Pro Ser Glu Arg
                100                 105                 110

Phe Ala Thr Pro Gly Phe Trp Phe Arg Cys Gly Ala Tyr Val Thr Ala
            115                 120                 125

Tyr Ala Gly Leu Thr Tyr Val Tyr Val Thr Lys Gly Ser Ser Leu Pro
130                 135                 140

Leu Cys Ile Ala Ile Gly Met Ser Gln Ala Ser Ile Gly Leu Asn Val
145                 150                 155                 160

Gln His Asp Ala Asn His Gly Ala Val Ser Ala Ser Pro Phe Trp Asn
                165                 170                 175

Asp Leu Leu Gly Phe Gly Ala Asp Met Ile Gly Gly Cys Lys Tyr Leu
            180                 185                 190

Trp Leu Gln Gln His Trp Thr His His Ala Phe Thr Asn Asp Ile Thr
            195                 200                 205

Arg Asp Pro Asp Ala Ser Ser Thr Asp Pro Phe Phe Leu Phe His Asp
210                 215                 220

Tyr Gly Lys Glu Thr Pro Val Arg Lys Ala Phe His Met Phe Gln His
225                 230                 235                 240

Phe Tyr Met Val Pro Val Leu Ala Met Tyr Trp Ala Ser Ser Ile Phe
            245                 250                 255

Asn Thr Asn Val Val Thr Leu Gln His Ala Gly Ala Ala Glu Gly Gly
            260                 265                 270

Met Lys Phe Ala Asn Ser Tyr Arg Glu Ala His Arg Pro Ile Ser Ile
            275                 280                 285

Ala Leu Arg Ser Leu Tyr Leu Gly Leu Tyr Cys Ala Thr Pro Phe Cys
            290                 295                 300

Trp His Ser Trp Pro Thr Ala Leu Ser His Val Trp Thr Met Ala Val
305                 310                 315                 320

Ser Glu Ser Leu Thr Leu Ala Ile Pro Phe Ala Leu Ser His Asn Phe
                325                 330                 335

Met Glu Ser Glu Arg His Pro Val Ala Asn Gly Gln Ala Cys Trp Tyr
            340                 345                 350

Lys Ala Gln Val Glu Thr Ser Ser Thr Tyr Gly Tyr Ile Ala Gly
            355                 360                 365

Trp Leu Thr Gly Gly Leu Asn Tyr Gln Ile Glu His His Leu Phe Pro
370                 375                 380

Arg Met Ser Ser Ala Trp Tyr Pro Tyr Ile Gln Pro Ala Val Arg Glu
385                 390                 395                 400

Val Cys Lys Lys His Gly Val Asn Tyr Val Tyr Tyr Pro Asn Ile Phe
                405                 410                 415
```

```
Ala Asn Leu Ala Ser Thr Phe Gln Tyr Ile Ala Gln Val Gly Gln Gly
            420                 425                 430

Ile Tyr Glu Arg Arg Val Lys Ala Ala
            435                 440

<210> SEQ ID NO 3
<211> LENGTH: 1326
<212> TYPE: DNA
<213> ORGANISM: Hemiselmis rufescens

<400> SEQUENCE: 3 atgccccca  acagcggcgc  gggaggcgcc  gcctccgacc  tccaggtctt  cccgtccgcc    60
gaccagctcc  ccgagggcta  cgtggcgatc  gacggcgagg  tctacgacct  caagggtttt   120
gaccaccccg  gggggagtc   catcctgctc  ttcggggga   acgatgtgtc  tgtgcagtat   180
cgcatgatcc  accccttca   cgcgggcaag  ggttcggtga  acaagatgaa  gaaggtgggc   240
aggctcgcaa  agtcgcgcct  cgactacact  tttgggagcg  agtttgagag  ggatctcgtg   300
gccgctgtcc  agaaggttgt  caagcccagc  cagcgcttcg  ctacccgcgg  cttttggttc   360
agatgcatct  tctacatctc  cctctacgcc  gtgctgacct  acttttacgt  ctcgaggggc   420
tcgagcatcg  cgctgtgcat  tgccatcggc  atgtctcagg  cctcaatcgg  ctaaacgtg   480 cagcacgacg  cgaatcacgg  cgccgtctcg  ccctccccgt  tttggaacga  ccttctgggc   540
ttcggggctg  acatgattgg  aggctgcaag  tatctgtggc  tgcagcagca  ctggacgcac   600
cacgccttca  ccaacgatat  cacgcgcgac  cctgatgcgt  cgagcacgga  cccctttttc   660
ctcttccacg  actatggcaa  gaatggggca  gtccgcaagg  cggtgcacgt  gttccagcac   720
ttctacatga  tccccgtgct  ggcaatgtac  tgggcatcct  ccatcttcaa  cacaaacgtc   780
gtcaccctgc  agcacacggg  cgccgccgac  gcgggcatga  agtttggcaa  ctcttaccgt   840
gaggcgcacc  gccccatctc  gatcctcctc  cgatccctct  acctcgctct  ctactgcgca   900
tctcccttct  accaccacca  ctgggccacg  cgctgctgc   atgtttggac  gatggcagtg   960
agtgagagcc  tcaccctcgc  catcccctt   gccctctcgc  acaactttct  ggagagcgag  1020
aggcaccctg  tcgccaacgg  ccaggtttgc  tggtacaagt  cacaggtgga  gacctcctcc  1080
acttacgggg  gctacgtcgc  ggggtggctg  acggggggc   tcaactttca  gattgagcac  1140
cacctcttcc  ctaggatgtc  ttctgcttgg  taccctaca   tccagccagc  cgtgcgcgaa  1200
gtatgcaaga  agcacggcgt  gaactatgtc  tactacccaa  acatcttcag  caaccttgtt  1260
tccaccttta  cctatattgc  tcaggttggg  agggggggcgt  acgaagggaa  ggtcaaagcc  1320
gactga                                                                   1326

<210> SEQ ID NO 4
<211> LENGTH: 441
<212> TYPE: PRT
<213> ORGANISM: Hemiselmis rufescens

<400> SEQUENCE: 4

Met Pro Pro Asn Ser Gly Ala Gly Gly Ala Ala Ser Asp Leu Gln Val
1               5                   10                  15

Phe Pro Ser Ala Asp Gln Leu Pro Glu Gly Tyr Val Ala Ile Asp Gly
            20                  25                  30

Glu Val Tyr Asp Leu Lys Gly Phe Asp His Pro Gly Gly Glu Ser Ile
        35                  40                  45

Leu Leu Phe Gly Gly Asn Asp Val Ser Val Gln Tyr Arg Met Ile His
    50                  55                  60
```

Pro Phe His Ala Gly Lys Gly Ser Val Asn Lys Met Lys Lys Val Gly
65                  70                  75                  80

Arg Leu Ala Lys Ser Arg Leu Asp Tyr Thr Phe Gly Ser Glu Phe Glu
                85                  90                  95

Arg Asp Leu Val Ala Val Gln Lys Val Lys Pro Ser Gln Arg
            100                 105                 110

Phe Ala Thr Arg Gly Phe Trp Phe Arg Cys Ile Phe Tyr Ile Ser Leu
            115                 120                 125

Tyr Ala Val Leu Thr Tyr Phe Tyr Val Ser Arg Gly Ser Ser Ile Ala
130                 135                 140

Leu Cys Ile Ala Ile Gly Met Ser Gln Ala Ser Ile Gly Leu Asn Val
145                 150                 155                 160

Gln His Asp Ala Asn His Gly Ala Val Ser Pro Ser Pro Phe Trp Asn
                165                 170                 175

Asp Leu Leu Gly Phe Gly Ala Asp Met Ile Gly Gly Cys Lys Tyr Leu
            180                 185                 190

Trp Leu Gln Gln His Trp Thr His His Ala Phe Thr Asn Asp Ile Thr
        195                 200                 205

Arg Asp Pro Asp Ala Ser Ser Thr Asp Pro Phe Leu Phe His Asp
210                 215                 220

Tyr Gly Lys Asn Gly Ala Val Arg Lys Ala Val His Val Phe Gln His
225                 230                 235                 240

Phe Tyr Met Ile Pro Val Leu Ala Met Tyr Trp Ala Ser Ser Ile Phe
                245                 250                 255

Asn Thr Asn Val Val Thr Leu Gln His Thr Gly Ala Ala Asp Ala Gly
                260                 265                 270

Met Lys Phe Gly Asn Ser Tyr Arg Glu Ala His Arg Pro Ile Ser Ile
            275                 280                 285

Leu Leu Arg Ser Leu Tyr Leu Ala Leu Tyr Cys Ala Ser Pro Phe Tyr
            290                 295                 300

His His His Trp Ala Thr Ala Leu Leu His Val Trp Thr Met Ala Val
305                 310                 315                 320

Ser Glu Ser Leu Thr Leu Ala Ile Pro Phe Ala Leu Ser His Asn Phe
                325                 330                 335

Leu Glu Ser Glu Arg His Pro Val Ala Asn Gly Gln Val Cys Trp Tyr
            340                 345                 350

Lys Ser Gln Val Glu Thr Ser Ser Thr Tyr Gly Gly Tyr Val Ala Gly
        355                 360                 365

Trp Leu Thr Gly Gly Leu Asn Phe Gln Ile Glu His His Leu Phe Pro
370                 375                 380

Arg Met Ser Ser Ala Trp Tyr Pro Tyr Ile Gln Pro Ala Val Arg Glu
385                 390                 395                 400

Val Cys Lys Lys His Gly Val Asn Tyr Val Tyr Tyr Pro Asn Ile Phe
                405                 410                 415

Ser Asn Leu Val Ser Thr Phe Thr Tyr Ile Ala Gln Val Gly Arg Gly
                420                 425                 430

Ala Tyr Glu Gly Lys Val Lys Ala Asp
            435                 440

<210> SEQ ID NO 5
<211> LENGTH: 1613
<212> TYPE: DNA
<213> ORGANISM: Hemiselmis virescens

<400> SEQUENCE: 5

```
ccacgcgtcc gcttgctcag aaatccccca gtcttcatgc ctcccaacag tggcgcggga    60
ggcgctgcct ccgacctcga ggtcttcccc tccgccgatg accttcccga ggggtacatc   120
gccatcgatg gggaggtcta cgacctcaag gggttcgacc accccggagg ggaatccatc   180
aatctcttcg ggggcaacga cgtttcggtg cagtatcgga tgatccatcc cttccatcag   240
ggcaaggggg ccgtcaacaa gatgaagaag gtgggcaggc tcgccagctc tcgcctcgac   300
tacaagtttg gcagcgactt cgagaaggat gttatcgccg ccgtcgccaa ggttgtcaaa   360
cccagcgagc gctttgcgac gcccggattc tggttccgct gcggtgctta cgtcactgct   420
tacgcggggc ttacctacgt gtacgtcacc aagggctcca gcctgcccct ctgcattgcc   480
attggcatgt ctcaggcctc aatcggccta acgtcagc acgatgcgaa tcacggcgct    540
gtgtccgctt ccccgttctg gaacgacctc ctgggcttcg gggcggacat gattgggga   600 tgcaagtacc tttggcttca gcagcactgg acgcaccacg cctttacaaa cgacattacc   660
cgtgaccccg acgcctcgag cacggacccc ttcttcctct tccacgacta tggcaaggag   720
actcccgtcc gcaaggcctt ccacatgttt cagcacttct acatggtgcc cgtgctcgcg   780
atgtactggg catcctcgat cttcaacacc aatgtcgtta cgctgcagca cgcgggcgcg   840 gcggagggg ggatgaagtt cgccaactcg taccgtgagg cgcaccgccc catctcgatc    900
gccctccgct cactctacct cggactctac tgcgcgaccc ccttctgctg cacagctgg    960 cccacggccc tctctcatgt gtggacgatg gctgtgtcgg agagcctcac ccttgccatc  1020
cccttgtcgc tttcccacaa ctttatggag agcgagaggc accggtggc aaacgggcag   1080 gcctgctggt acaaggcgca ggtcgagacg tcttcgacgt atgggggggta catcgctggg  1140 tggctcacgg ggggcctcaa ctaccagatt gagcaccacc tgttccccag gatgtcatcg  1200
gcttggtacc cctacatcca gcccgcggtg cgcgaggtct gcaagaagca cggcgtaaac  1260
tacgtctatt acccaaacat atttgccaac ctcgcctcca cgttccagta cattgcgcag  1320
gtgggccagg ggatctatga gaggagggtc aaggcggcct gatcacgcgg tccgacgtcc  1380
gaccaaaggg gtctgacgcc tgaccccaga cccgcgtgcc gtgcgccggg gggcggggg   1440 cctgcgctct gggtgctcag ggggggggg gggggggggt aggcgccccg gcgtagggcc   1500
gcaaggctgc gtgcgcgtta ggtcccgggg cgtgggtgga ttctgggtc caagggctgc   1560 taatgagttg ccaagtgcta ctacagagtt gctcgggaaa aaaaaaaaa aag          1613
```

<210> SEQ ID NO 6
<211> LENGTH: 30
<212> TYPE: DNA
<213> ORGANISM: Artificial Sequence
<220> FEATURE:
<223> OTHER INFORMATION: Primer

<400> SEQUENCE: 6

```
gtcgacaaac aatgcctccc aacagtggcg                                     30
```

<210> SEQ ID NO 7
<211> LENGTH: 27
<212> TYPE: DNA
<213> ORGANISM: Artificial Sequence
<220> FEATURE:
<223> OTHER INFORMATION: Primer

<400> SEQUENCE: 7

```
cctgcaggtc aggccgcctt gaccctc                                        27
```

```
<210> SEQ ID NO 8
<211> LENGTH: 38
<212> TYPE: DNA
<213> ORGANISM: Artificial Sequence
<220> FEATURE:
<223> OTHER INFORMATION: Primer

<400> SEQUENCE: 8
cagtcgacaa acaatgcccc ccaacagcgg cgcgggag                              38

<210> SEQ ID NO 9
<211> LENGTH: 35
<212> TYPE: DNA
<213> ORGANISM: Artificial Sequence
<220> FEATURE:
<223> OTHER INFORMATION: Primer

<400> SEQUENCE: 9
cacctgcagg tcagtcggct ttgaccttcc cttcg                                 35

<210> SEQ ID NO 10
<211> LENGTH: 456
<212> TYPE: PRT
<213> ORGANISM: Pythium irregulare

<400> SEQUENCE: 10
```

| Met | Gly | Thr | Asp | Gln | Gly | Lys | Thr | Phe | Thr | Trp | Gln | Glu | Val | Ala | Lys |
|---|---|---|---|---|---|---|---|---|---|---|---|---|---|---|---|
| 1 | | | | 5 | | | | | 10 | | | | | 15 | |

His Asn Thr Ala Lys Ser Ala Trp Val Ile Ile Arg Gly Glu Val Tyr
            20                  25                  30

Asp Val Thr Glu Trp Ala Asp Lys His Pro Gly Gly Ser Glu Leu Ile
        35                  40                  45

Val Leu His Ser Gly Arg Glu Cys Thr Asp Thr Phe Tyr Ser Tyr His
    50                  55                  60

Pro Phe Ser Asn Arg Ala Asp Lys Ile Leu Ala Lys Tyr Lys Ile Gly
65                  70                  75                  80

Lys Leu Val Gly Gly Tyr Glu Phe Pro Val Phe Lys Pro Asp Ser Gly
                85                  90                  95

Phe Tyr Lys Glu Cys Ser Glu Arg Val Ala Glu Tyr Phe Lys Thr Asn
            100                 105                 110

Asn Leu Asp Pro Lys Ala Ala Phe Ala Gly Leu Trp Arg Met Val Phe
        115                 120                 125

Val Phe Ala Val Ala Ala Leu Ala Tyr Met Gly Met Asn Glu Leu Ile
    130                 135                 140

Pro Gly Asn Val Tyr Ala Gln Tyr Ala Trp Gly Val Val Phe Gly Val
145                 150                 155                 160

Phe Gln Ala Leu Pro Leu Leu His Val Met His Asp Ser Ser His Ala
                165                 170                 175

Ala Cys Ser Ser Pro Ala Met Trp Gln Ile Ile Gly Arg Gly Val
            180                 185                 190

Met Asp Trp Phe Ala Gly Ala Ser Met Val Ser Trp Leu Asn Gln His
        195                 200                 205

Val Val Gly His His Ile Tyr Thr Asn Val Ala Gly Ala Asp Pro Asp
    210                 215                 220

Leu Pro Val Asp Phe Glu Ser Asp Val Arg Arg Ile Val His Arg Gln
225                 230                 235                 240

Val Leu Leu Pro Ile Tyr Lys Phe Gln His Ile Tyr Leu Pro Pro Leu
                245                 250                 255

Tyr Gly Val Leu Gly Leu Lys Phe Arg Ile Gln Asp Val Phe Glu Thr

```
                260                 265                 270
Phe Val Ser Leu Thr Asn Gly Pro Val Arg Val Asn Pro His Pro Val
            275                 280                 285

Ser Asp Trp Val Gln Met Ile Phe Ala Lys Ala Phe Trp Thr Phe Tyr
        290                 295                 300

Arg Ile Tyr Ile Pro Leu Val Trp Leu Lys Ile Thr Pro Ser Thr Phe
305                 310                 315                 320

Trp Gly Val Phe Phe Leu Ala Glu Phe Thr Thr Gly Trp Tyr Leu Ala
                325                 330                 335

Phe Asn Phe Gln Val Ser His Val Ser Thr Glu Cys Glu Tyr Pro Cys
            340                 345                 350

Gly Asp Ala Pro Ser Ala Glu Val Gly Asp Glu Trp Ala Ile Ser Gln
        355                 360                 365

Val Lys Ser Ser Val Asp Tyr Ala His Gly Ser Pro Leu Ala Ala Phe
    370                 375                 380

Leu Cys Gly Ala Leu Asn Tyr Gln Val Thr His His Leu Tyr Pro Gly
385                 390                 395                 400

Ile Ser Gln Tyr His Tyr Pro Ala Ile Ala Pro Ile Ile Ile Asp Val
                405                 410                 415

Cys Lys Lys Tyr Asn Ile Lys Tyr Thr Val Leu Pro Thr Phe Thr Glu
            420                 425                 430

Ala Leu Leu Ala His Phe Lys His Leu Lys Asn Met Gly Glu Leu Gly
        435                 440                 445

Lys Pro Val Glu Ile His Met Gly
    450                 455

<210> SEQ ID NO 11
<211> LENGTH: 446
<212> TYPE: PRT
<213> ORGANISM: Mortierella alpina

<400> SEQUENCE: 11

Met Gly Thr Asp Gln Gly Lys Thr Phe Thr Trp Glu Glu Leu Ala Ala
1               5                   10                  15

His Asn Thr Lys Asp Asp Leu Leu Leu Ala Ile Arg Gly Arg Val Tyr
            20                  25                  30

Asp Val Thr Lys Phe Leu Ser Arg His Pro Gly Gly Val Asp Thr Leu
        35                  40                  45

Leu Leu Gly Ala Gly Arg Asp Val Thr Pro Val Phe Glu Met Tyr His
    50                  55                  60

Ala Phe Gly Ala Ala Asp Ala Ile Met Lys Lys Tyr Tyr Val Gly Thr
65                  70                  75                  80

Leu Val Ser Asn Glu Leu Pro Ile Phe Pro Glu Pro Thr Val Phe His
                85                  90                  95

Lys Thr Ile Lys Thr Arg Val Glu Gly Tyr Phe Thr Asp Arg Asn Ile
            100                 105                 110

Asp Pro Lys Asn Arg Pro Glu Ile Trp Gly Arg Tyr Ala Leu Ile Phe
        115                 120                 125

Gly Ser Leu Ile Ala Ser Tyr Tyr Ala Gln Leu Phe Val Pro Phe Val
    130                 135                 140

Val Glu Arg Thr Trp Leu Gln Val Val Phe Ala Ile Ile Met Gly Phe
145                 150                 155                 160

Ala Cys Ala Gln Val Gly Leu Asn Pro Leu His Asp Ala Ser His Phe
                165                 170                 175

Ser Val Thr His Asn Pro Thr Val Trp Lys Ile Leu Gly Ala Thr His
```

```
                180             185                 190
Asp Phe Phe Asn Gly Ala Ser Tyr Leu Val Trp Met Tyr Gln His Met
            195                 200                 205
Leu Gly His His Pro Tyr Thr Asn Ile Ala Gly Ala Asp Pro Asp Val
        210                 215                 220
Ser Thr Ser Glu Pro Asp Val Arg Arg Ile Lys Pro Asn Gln Lys Trp
225                 230                 235                 240
Phe Val Asn His Ile Asn Gln His Met Phe Val Pro Phe Leu Tyr Gly
                245                 250                 255
Leu Leu Ala Phe Lys Val Arg Ile Gln Asp Ile Asn Ile Leu Tyr Phe
            260                 265                 270
Val Lys Thr Asn Asp Ala Ile Arg Val Asn Pro Ile Ser Thr Trp His
        275                 280                 285
Thr Val Met Phe Trp Gly Gly Lys Ala Phe Phe Val Trp Tyr Arg Leu
    290                 295                 300
Ile Val Pro Leu Gln Tyr Leu Pro Leu Gly Lys Val Leu Leu Leu Phe
305                 310                 315                 320
Thr Val Ala Asp Met Val Ser Ser Tyr Trp Leu Ala Leu Thr Phe Gln
                325                 330                 335
Ala Asn His Val Val Glu Glu Val Gln Trp Pro Leu Pro Asp Glu Asn
            340                 345                 350
Gly Ile Ile Gln Lys Asp Trp Ala Ala Met Gln Val Glu Thr Thr Gln
        355                 360                 365
Asp Tyr Ala His Asp Ser His Leu Trp Thr Ser Ile Thr Gly Ser Leu
    370                 375                 380
Asn Tyr Gln Ala Val His His Leu Phe Pro Asn Val Ser Gln His His
385                 390                 395                 400
Tyr Pro Asp Ile Leu Ala Ile Ile Lys Asn Thr Cys Ser Glu Tyr Lys
                405                 410                 415
Val Pro Tyr Leu Val Lys Asp Thr Phe Trp Gln Ala Phe Ala Ser His
            420                 425                 430
Leu Glu His Leu Arg Val Leu Gly Leu Arg Pro Lys Glu Glu
        435                 440                 445

<210> SEQ ID NO 12
<211> LENGTH: 457
<212> TYPE: PRT
<213> ORGANISM: Mortierella alpina

<400> SEQUENCE: 12

Met Ala Ala Ala Pro Ser Val Arg Thr Phe Thr Arg Ala Glu Val Leu
1               5                   10                  15
Asn Ala Glu Ala Leu Asn Glu Gly Lys Lys Asp Ala Glu Ala Pro Phe
                20                  25                  30
Leu Met Ile Ile Asp Asn Lys Val Tyr Asp Val Arg Glu Phe Val Pro
            35                  40                  45
Asp His Pro Gly Gly Ser Val Ile Leu Thr His Val Gly Lys Asp Gly
        50                  55                  60
Thr Asp Val Phe Asp Thr Phe His Pro Glu Ala Ala Trp Glu Thr Leu
65                  70                  75                  80
Ala Asn Phe Tyr Val Gly Asp Ile Asp Glu Ser Asp Arg Asp Ile Lys
                85                  90                  95
Asn Asp Asp Phe Ala Ala Glu Val Arg Lys Leu Arg Thr Leu Phe Gln
            100                 105                 110
Ser Leu Gly Tyr Tyr Asp Ser Ser Lys Ala Tyr Tyr Ala Phe Lys Val
```

```
            115                 120                 125
Ser Phe Asn Leu Cys Ile Trp Gly Leu Ser Thr Val Ile Val Ala Lys
130                 135                 140

Trp Gly Gln Thr Ser Thr Leu Ala Asn Val Leu Ser Ala Ala Leu Leu
145                 150                 155                 160

Gly Leu Phe Trp Gln Gln Cys Gly Trp Leu Ala His Asp Phe Leu His
                165                 170                 175

His Gln Val Phe Gln Asp Arg Phe Trp Gly Asp Leu Phe Gly Ala Phe
            180                 185                 190

Leu Gly Gly Val Cys Gln Gly Phe Ser Ser Ser Trp Trp Lys Asp Lys
        195                 200                 205

His Asn Thr His His Ala Ala Pro Asn Val His Gly Glu Asp Pro Asp
    210                 215                 220

Ile Asp Thr His Pro Leu Leu Thr Trp Ser Glu His Ala Leu Glu Met
225                 230                 235                 240

Phe Ser Asp Val Pro Asp Glu Glu Leu Thr Arg Met Trp Ser Arg Phe
                245                 250                 255

Met Val Leu Asn Gln Thr Trp Phe Tyr Phe Pro Ile Leu Ser Phe Ala
            260                 265                 270

Arg Leu Ser Trp Cys Leu Gln Ser Ile Leu Phe Val Leu Pro Asn Gly
        275                 280                 285

Gln Ala His Lys Pro Ser Gly Ala Arg Val Pro Ile Ser Leu Val Glu
    290                 295                 300

Gln Leu Ser Leu Ala Met His Trp Thr Trp Tyr Leu Ala Thr Met Phe
305                 310                 315                 320

Leu Phe Ile Lys Asp Pro Val Asn Met Leu Val Tyr Phe Leu Val Ser
                325                 330                 335

Gln Ala Val Cys Gly Asn Leu Leu Ala Ile Val Phe Ser Leu Asn His
            340                 345                 350

Asn Gly Met Pro Val Ile Ser Lys Glu Glu Ala Val Asp Met Asp Phe
        355                 360                 365

Phe Thr Lys Gln Ile Ile Thr Gly Arg Asp Val His Pro Gly Leu Phe
    370                 375                 380

Ala Asn Trp Phe Thr Gly Gly Leu Asn Tyr Gln Ile Glu His His Leu
385                 390                 395                 400

Phe Pro Ser Met Pro Arg His Asn Phe Ser Lys Ile Gln Pro Ala Val
                405                 410                 415

Glu Thr Leu Cys Lys Lys Tyr Asn Val Arg Tyr His Thr Thr Gly Met
            420                 425                 430

Ile Glu Gly Thr Ala Glu Val Phe Ser Arg Leu Asn Glu Val Ser Lys
        435                 440                 445

Ala Ala Ser Lys Met Gly Lys Ala Gln
    450                 455

<210> SEQ ID NO 13
<211> LENGTH: 482
<212> TYPE: PRT
<213> ORGANISM: Thalassiosira pseudonana

<400> SEQUENCE: 13

Met Pro Pro Asn Ala Glu Val Lys Asn Leu Arg Ser Arg Ser Ile Pro
1               5                   10                  15

Thr Lys Lys Ser Ser Ser Ser Ser Thr Ala Asn Asp Asp Pro Ala
            20                  25                  30

Thr Gln Ser Thr Ser Pro Val Asn Arg Thr Leu Lys Ser Leu Asn Gly
```

```
                35                  40                  45
Asn Glu Ile Ala Ile Asp Gly Val Ile Tyr Asp Ile Asp Gly Phe Val
            50                  55                  60
His Pro Gly Gly Glu Val Ile Ser Phe Phe Gly Asn Asp Val Thr
 65                  70                  75                  80
Val Gln Tyr Lys Met Ile His Pro Tyr His Asn Ser Lys His Leu Glu
                85                  90                  95
Lys Met Arg Ala Val Gly Lys Ile Ala Asp Tyr Ser Thr Glu Tyr Lys
                100                 105                 110
Phe Asp Thr Pro Phe Glu Arg Glu Ile Lys Ser Glu Val Phe Lys Ile
                115                 120                 125
Val Arg Arg Gly Arg Glu Phe Gly Thr Thr Gly Tyr Phe Leu Arg Ala
                130                 135                 140
Phe Phe Tyr Ile Ala Leu Phe Phe Thr Met Gln Tyr Thr Phe Ala Thr
145                 150                 155                 160
Cys Thr Thr Phe Thr Thr Tyr Asp His Trp Tyr Gln Ser Gly Val Phe
                165                 170                 175
Ile Ala Ile Val Phe Gly Ile Ser Gln Ala Phe Ile Gly Leu Asn Val
                180                 185                 190
Gln His Asp Ala Asn His Gly Ala Ala Ser Lys Arg Pro Trp Val Asn
                195                 200                 205
Asp Leu Leu Gly Ser Gly Ala Asp Leu Ile Gly Gly Cys Lys Trp Asn
                210                 215                 220
Trp Leu Ala Gln His Trp Thr His His Ala Tyr Thr Asn His Ala Asp
225                 230                 235                 240
Lys Asp Pro Asp Ser Phe Ser Ser Glu Pro Val Phe Asn Phe Asn Asp
                245                 250                 255
Tyr Pro Ile Gly His Pro Lys Arg Lys Trp Trp His Arg Phe Gln Gly
                260                 265                 270
Leu Tyr Phe Leu Ile Met Leu Ser Phe Tyr Trp Val Ser Met Val Phe
                275                 280                 285
Asn Pro Gln Val Ile Asp Leu Arg His Ala Gly Ala Ala Tyr Val Gly
                290                 295                 300
Phe Gln Met Glu Asn Asp Phe Ile Val Lys Arg Arg Lys Tyr Ala Met
305                 310                 315                 320
Ala Leu Arg Ala Met Tyr Phe Tyr Phe Asn Ile Tyr Cys Pro Ile Val
                325                 330                 335
Asn Asn Gly Leu Thr Trp Ser Thr Val Gly Ile Ile Leu Leu Met Gly
                340                 345                 350
Val Ser Glu Ser Phe Met Leu Ser Gly Leu Phe Val Leu Ser His Asn
                355                 360                 365
Phe Glu Asn Ser Glu Arg Asp Pro Thr Ser Glu Tyr Arg Lys Thr Gly
                370                 375                 380
Glu Gln Val Cys Trp Phe Lys Ser Gln Val Glu Thr Ser Ser Thr Tyr
385                 390                 395                 400
Gly Gly Ile Val Ala Gly Cys Leu Thr Gly Gly Leu Asn Phe Gln Val
                405                 410                 415
Glu His His Leu Phe Pro Arg Met Ser Ser Ala Trp Tyr Pro Phe Ile
                420                 425                 430
Ala Pro Lys Val Arg Glu Ile Cys Lys Lys His Gly Val Arg Tyr Ala
                435                 440                 445
Tyr Tyr Pro Tyr Ile Trp Gln Asn Leu His Ser Thr Val Ser Tyr Met
                450                 455                 460
```

His Gly Thr Gly Thr Gly Ala Arg Trp Glu Leu Gln Pro Leu Ser Gly
465                 470                 475                 480

Arg Ala

<210> SEQ ID NO 14
<211> LENGTH: 463
<212> TYPE: PRT
<213> ORGANISM: Peridinium sp. CCMP626

<400> SEQUENCE: 14

Met Ala Pro Asp Ala Asp Lys Leu Arg Gln Arg Lys Ala Gln Ser Ile
1               5                   10                  15

Gln Asp Thr Ala Asp Ser Gln Ala Thr Glu Leu Lys Ile Gly Thr Leu
            20                  25                  30

Lys Gly Leu Gln Gly Thr Glu Ile Val Ile Asp Gly Asp Ile Tyr Asp
        35                  40                  45

Ile Lys Asp Phe Asp His Pro Gly Gly Glu Ser Ile Met Thr Phe Gly
    50                  55                  60

Gly Asn Asp Val Thr Ala Thr Tyr Lys Met Ile His Pro Tyr His Ser
65                  70                  75                  80

Lys His His Leu Glu Lys Met Lys Lys Val Gly Arg Val Pro Asp Tyr
                85                  90                  95

Thr Ser Glu Tyr Lys Phe Asp Thr Pro Phe Glu Arg Glu Ile Lys Gln
            100                 105                 110

Glu Val Phe Lys Ile Val Arg Arg Gly Arg Glu Phe Gly Thr Pro Gly
        115                 120                 125

Tyr Phe Phe Arg Ala Phe Cys Tyr Ile Gly Leu Phe Phe Tyr Leu Gln
130                 135                 140

Tyr Leu Trp Val Thr Thr Pro Thr Thr Phe Ala Leu Ala Ile Phe Tyr
145                 150                 155                 160

Gly Val Ser Gln Ala Phe Ile Gly Leu Asn Val Gln His Asp Ala Asn
                165                 170                 175

His Gly Ala Ala Ser Lys Lys Pro Trp Ile Asn Asn Leu Leu Gly Leu
            180                 185                 190

Gly Ala Asp Phe Ile Gly Gly Ser Lys Trp Leu Trp Met Asn Gln His
        195                 200                 205

Trp Thr His His Thr Tyr Thr Asn His His Glu Lys Asp Pro Asp Ala
210                 215                 220

Leu Gly Ala Glu Pro Met Leu Leu Phe Asn Asp Tyr Pro Leu Gly His
225                 230                 235                 240

Pro Lys Arg Thr Leu Ile His His Phe Gln Ala Phe Tyr Tyr Leu Phe
                245                 250                 255

Val Leu Ala Gly Tyr Trp Val Ser Ser Val Phe Asn Pro Gln Ile Leu
            260                 265                 270

Asp Leu Gln His Arg Gly Ala Gln Ala Val Gly Met Lys Met Glu Asn
        275                 280                 285

Asp Tyr Ile Ala Lys Ser Arg Lys Tyr Ala Ile Phe Leu Arg Leu Leu
290                 295                 300

Tyr Ile Tyr Thr Asn Ile Val Ala Pro Ile Gln Asn Gln Gly Phe Ser
305                 310                 315                 320

Leu Thr Val Val Ala His Ile Leu Thr Met Gly Val Ala Ser Ser Leu
                325                 330                 335

Thr Leu Ala Thr Leu Phe Ala Leu Ser His Asn Phe Glu Asn Ala Asp
            340                 345                 350

Arg Asp Pro Thr Tyr Glu Ala Arg Lys Gly Gly Glu Pro Val Cys Trp

-continued

```
                355                 360                 365
Phe Lys Ser Gln Val Glu Thr Ser Ser Thr Tyr Gly Gly Phe Ile Ser
    370                 375                 380

Gly Cys Leu Thr Gly Gly Leu Asn Phe Gln Val Glu His His Leu Phe
385                 390                 395                 400

Pro Arg Met Ser Ser Ala Trp Tyr Pro Tyr Ile Ala Pro Thr Val Arg
                405                 410                 415

Glu Val Cys Lys Lys His Gly Val Lys Tyr Ala Tyr Tyr Pro Trp Val
            420                 425                 430

Trp Gln Asn Leu Ile Ser Thr Val Lys Tyr Leu His Gln Ser Gly Thr
        435                 440                 445

Gly Ser Asn Trp Lys Asn Gly Ala Asn Pro Tyr Ser Gly Lys Leu
    450                 455                 460

<210> SEQ ID NO 15
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 15

Leu Phe Gly Gly Asn Asp Val Ser Val Gln Tyr Arg Met Ile
1               5                   10

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 16

Ile Ala Ile Gly Met Ser Gln Ala Ser Ile Gly Leu Asn Val Gln
1               5                   10                  15

<210> SEQ ID NO 17
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 17

Gly Ala Asp Met Ile Gly Gly Cys Lys Tyr Leu Trp Leu Gln
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 18

Ala Ser Ser Thr Asp Pro Phe Phe Leu Phe His Asp Tyr Gly Lys
1               5                   10                  15

<210> SEQ ID NO 19
<211> LENGTH: 19
<212> TYPE: PRT
<213> ORGANISM: Artificial Sequence
<220> FEATURE:
<223> OTHER INFORMATION: Synthetic Peptide
```

```
<400> SEQUENCE: 19

Leu Ala Met Tyr Trp Ala Ser Ser Ile Phe Asn Thr Asn Val Val Thr
1               5                   10                  15

Leu Gln His

<210> SEQ ID NO 20
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 20

Asn Ser Tyr Arg Glu Ala His Arg Pro Ile Ser Ile
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 21

His Val Trp Thr Met Ala Val Ser Glu Ser Leu Thr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 22

Leu Ala Ile Pro Phe Ala Leu Ser His Asn Phe
1               5                   10

<210> SEQ ID NO 23
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 23

Gln Pro Ala Val Arg Glu Val Cys Lys Lys His Gly Val Asn Tyr Val
1               5                   10                  15

<210> SEQ ID NO 24
<211> LENGTH: 4
<212> TYPE: PRT
<213> ORGANISM: Artificial sequence
<220> FEATURE:
<223> OTHER INFORMATION: Synthetic peptide

<400> SEQUENCE: 24

His Pro Gly Gly
1

<210> SEQ ID NO 25
<211> LENGTH: 5
<212> TYPE: PRT
<213> ORGANISM: Artificial sequence
<220> FEATURE:
<223> OTHER INFORMATION: Synthetic peptide
<220> FEATURE:
```

```
-continued

<221> NAME/KEY: MISC_FEATURE
<222> LOCATION: (2)..(3)
<223> OTHER INFORMATION: Xaa is any amino acid

<400> SEQUENCE: 25

Gln Xaa Xaa His His
1               5
```

UTILIZATION OF FATTY ACID DESATURASES FROM *HEMISELMIS SPP*

REFERENCE TO RELATED APPLICATIONS

This application claims priority to U.S. Provisional Application No. 61/105,316, filed on Oct. 14, 2008, which is incorporated herein by reference in its entirety.

INCORPORATION OF SEQUENCE LISTING

The Sequence Listing, which is a part of the present disclosure, includes a computer readable 36 KB file entitled "MONS219US_ST25.txt" comprising nucleotide and/or amino acid sequences of the present invention submitted via EFS-Web. The subject matter of the Sequence Listing is incorporated herein by reference in its entirety.

BACKGROUND OF THE INVENTION

1. Field of the Invention

The invention relates generally to desaturase enzymes that modulate the number and location of double bonds in long chain poly-unsaturated fatty acids (LC-PUFA's). In particular, the invention relates to the alteration of fatty acid profiles using delta 5 desaturase enzymes and nucleic acids encoding such desaturase enzymes.

2. Description of the Related Art

The primary products of fatty acid biosynthesis in most organisms are 16- and 18-carbon compounds. The relative proportion of chain lengths and degree of unsaturation of these fatty acids vary widely among species. Mammals, for example, produce primarily saturated and monounsaturated fatty acids, while most higher plants produce fatty acids with one, two, or three double bonds, the latter two comprising polyunsaturated fatty acids (PUFA's).

Two main families of PUFAs are the omega-3 fatty acids (also represented as "n-3" fatty acids), exemplified by eicosapentaenoic acid (EPA, 20:5, n-3) and the omega-6 fatty acids (also represented as "n-6" fatty acids), exemplified by arachidonic acid (ARA, 20:4, n-6). PUFAs are important components of the plasma membrane of the cell and adipose tissue, where they may be found in such forms as phospholipids and as triglycerides, respectively. PUFAs are necessary for proper development in mammals, particularly in the developing infant brain, and for tissue formation and repair. Arachidonic acid is the principal precursor for the synthesis of eicosanoids, which include leukotrienes, prostaglandins, and thromboxanes, and which also play a significant role in the inflammation process.

Several disorders respond to treatment with fatty acids. Supplementation with PUFAs has been shown to reduce the rate of restenosis after angioplasty. Evidence indicates that PUFAs may be involved in calcium metabolism, suggesting that PUFAs may be useful in the treatment or prevention of osteoporosis and of kidney or urinary tract stones. The majority of evidence for health benefits applies to the long chain omega-3 fats, eicosapentaenoic acid and docosahexaenoic acid (DHA, 22:6, n-3) which are found in fish and fish oil.

PUFAs, such as linoleic acid (LA, 18:2, Δ9, 12) and α-linolenic acid (ALA, 18:3, Δ9, 12, 15), are regarded as essential fatty acids in the diet because mammals lack the ability to synthesize these acids. LA is produced from oleic acid (OA, 18:1, Δ9) by a Δ12-desaturase while ALA is produced from LA by a Δ15-desaturase. However, when ingested, mammals have the ability to metabolize LA and ALA to form the n-6 and n-3 families of long-chain polyunsaturated fatty acids (LC-PUFA). In mammals, the formation of LC-PUFA is rate-limited by the step of Δ6 desaturation, which converts LA to GLA and ALA to SDA. Many physiological and pathological conditions have been shown to depress this metabolic step even further, and consequently, the production of LC-PUFA. To overcome the rate-limiting step and increase tissue levels of EPA, one could consume large amounts of ALA. Alternatively, bypassing the Δ6-desaturation via dietary supplementation with EPA or DHA can effectively alleviate many pathological diseases associated with low levels of PUFA. However, as set forth in more detail below, currently available sources of PUFA are not desirable.

Major long chain PUFAs of importance include DHA and EPA, which are primarily found in different types of fish oil, and ARA, found in filamentous fungi such as *Mortierella*. For DHA, a number of sources exist for commercial production including a variety of marine organisms, oils obtained from cold water marine fish, and egg yolk fractions. However, there are several disadvantages associated with commercial production of PUFAs from natural sources. Natural sources of PUFAs tend to have highly heterogeneous oil compositions. The oils obtained from these sources therefore can require extensive purification to separate out one or more desired PUFAs or to produce an oil which is enriched in one or more PUFAs.

Other natural limitations favor a novel approach for the production of PUFAs. Weather and disease can cause fluctuation in yields from both fish and other marine sources. Large-scale fermentation of organisms such as *Mortierella* is expensive. Natural animal tissues contain low amounts of ARA and are difficult to process.

SUMMARY OF THE INVENTION

One aspect of the current invention provides isolated nucleic acids encoding a polypeptide capable of desaturating a fatty acid molecule at carbon 5. These nucleic acids may be used to transform cells or modify the fatty acid composition of a plant or the oil produced by a plant. Certain embodiments of the current invention provide isolated polynucleotide sequences isolated from *Hemiselmis* spp. having a unique desaturase activity. In certain further embodiments of the invention, the polynucleotides encode a polypeptide having at least 75% sequence identity to the polypeptide sequence of SEQ ID NO:2 or SEQ ID NO:4, including at least about 80%, 82%, 85%, 87%, 90%, 92%, 95%, 98% and 99% identity to these sequences. Those of skill in the art will recognize that, as these sequences are related, a given polypeptide may simultaneously share 75% or greater sequence identity to more than one of these polypeptide sequences. In certain embodiments, a *Hemiselmis* spp. desaturase of the invention is further defined as an omega-3 Δ5 desaturase (i.e., a desaturase with an omega-3 substrate preference).

In another aspect, the invention provides an isolated polynucleotide that encodes a polypeptide having desaturase activity that desaturates a fatty acid molecule at carbon 5, comprising a sequence selected from the group consisting of: (a) a polynucleotide encoding the polypeptide of SEQ ID NO:2 or SEQ ID NO:4; (b) a polynucleotide comprising the nucleic acid sequence of SEQ ID NO:1 or SEQ ID NO:3; (c) a polynucleotide hybridizing to SEQ ID NO:1 or SEQ ID NO:3, or a complement thereof, under conditions of 5×SSC, 50% formamide and 42° C.; (d) a polynucleotide encoding a polypeptide with at least 75%, 85%, 95%, 98%, or 99% sequence identity to a polypeptide sequence of SEQ ID NO:2 or SEQ ID NO:4; and e) a polynucleotide encoding a polypeptide having at least one of the amino acid motifs:

LeuPheGlyGlyAsnAspValSerValGlnTyrArgMetIle (LFGGNDVSVQYRMI) (SEQ ID NO: 15); IleAlaIleGlyMetSerGlnAlaSerIleGlyLeuAsnValGln (IAIGMSQASIGLNVQ) (SEQ ID NO: 16); GlyAlaAspMetIleGlyGlyCysLysTyrLeuTrpLeuGln (GADMIGGCKYLWLQ) (SEQ ID NO:17); AlaSerSerThrAspProPhePheLeuPheHisAspTyrGlyLys (ASSTDPFFLFHDYGK) (SEQ ID NO: 18); LeuAlaMetTyrTrpAlaSerSerIlePheAsnThrAsnValValThrLeuGlnHis (LAMYWASSIFNTNVVTLQH) (SEQ ID NO: 19); AsnSerTyrArgGluAlaHisArgProIleSerIle (NSYREAHRPISI) (SEQ ID NO: 20); HisValTrpThrMetAlaValSerGluSerLeuThr (HVWTMAVSESLT) (SEQ ID NO: 21); LeuAlaIleProPheAlaLeuSerHisAsnPhe (LAIPFALSHNF) (SEQ ID NO:22); or GlnProAlaValArgGluValCysLysLysHisGlyValAsnTyrVal (QPAVREVCKKHGVNYV) (SEQ ID NO: 23). In another aspect, the invention provides an isolated polypeptide comprising the polypeptide sequences of SEQ ID NO:2 or SEQ ID NO:4 or a fragment thereof having desaturase activity that desaturates a fatty acid molecule at carbon 5.

In yet another aspect, the invention provides a DNA construct comprising the isolated polynucleotide that encodes a polypeptide having desaturase activity that desaturates a fatty acid molecule at carbon 5, comprising a sequence selected from the group consisting of: (a) a polynucleotide encoding the polypeptide of SEQ ID NO:2 or SEQ ID NO:4; (b) a polynucleotide comprising the nucleic acid sequence of SEQ ID NO:1 or SEQ ID NO:3; (c) a polynucleotide hybridizing to SEQ ID NO:1 or SEQ ID NO:3, or a complement thereof, under conditions of 5×SSC, 50% formamide and 42° C.; and (d) a polynucleotide encoding a polypeptide with at least 75%, 85%, 95%, 98%, or 99% sequence identity to a polypeptide sequence of SEQ ID NO:2 or SEQ ID NO:4. In a further embodiment, the DNA construct further comprises a heterologous promoter operably linked to the isolated polynucleotide described above. In other embodiments, the promoter is functional in a prokaryotic cell or in a eukaryotic cell. In certain embodiments, the eukaryotic cell in which the promoter is functional is a plant cell. In a further embodiment, the promoter is a seed-enhanced promoter. Examples of seed-enhanced promoters include, but are not limited to, the USP88 promoter, the 7Sα promoter, the 7Sα' promoter, the Arcelin-5 promoter, the napin promoter and the oleosin promoter. In yet another embodiment, the DNA construct further comprises at least one additional polynucleotide sequence encoding a fatty acid elongase.

In still yet another aspect, the invention provides a host cell transformed with a DNA construct comprising the isolated polynucleotide that encodes a polypeptide having desaturase activity that desaturates a fatty acid molecule at carbon 5 provided by the invention. The host cell may be a plant, animal, fungal or bacterial cell. In a further embodiment, the host cell of the invention provides a host cell that exhibits altered fatty acid biosynthesis relative to a cell of the same genotype as the host cell but lacking the DNA construct. For example, a transformed host cell of the invention may comprise an elevated level of EPA relative to AA content, such as about 2- or about 3-fold more EPA than AA. In yet another aspect, the host cell has inherited the DNA construct from a progenitor of the cell.

In still yet another aspect, the invention provides a plant and its progeny comprising the host cells transformed with a DNA construct of the invention. Such a plant may be defined as comprising altered fatty acid metabolism relative to a plant of the same genotype lacking the DNA construct. In one embodiment, the invention provides a transgenic plant or part thereof comprising an omega-3 Δ5 desaturase (i.e., a desaturase with an omega-3 substrate preference). In yet another aspect, such a plant may further comprise at least one additional polynucleotide sequence encoding a fatty acid elongase. In one embodiment, the plant is selected from the group consisting of canola, *Brassica campestris*, oilseed rape, rapeseed, soybean, crambe, mustard, castor bean, peanut, sesame, cottonseed, linseed, safflower, oil palm, flax, sunflower, corn, rice, barley, millet, rye, wheat, oat, alfalfa and sorghum. The invention also provides seed of the plant of the invention, such as a seed having an altered fatty acid content relative to seed that does not comprise the a DNA construct of the invention. For example, a seed of the invention may comprise an elevated level of EPA relative to AA content, such as about 2- or about 3-fold more EPA than AA.

In still a further aspect, there is provided a transformed cell, transgenic plant or part thereof comprising a polynucleotide molecule encoding a Δ5 desaturase of the invention operably linked to a heterologous promoter and at least one additional polynucleotide molecule encoding a fatty acid elongase or desaturase enzyme. In certain embodiments, an additional fatty acid elongase or desaturase may be a Δ6 desaturase, a Δ6 elongase (e.g., *M. alpina* Δ6 elongase), a Δ18 elongase, a Δ15 desaturase, a Δ9 elongase, a Δ8 desaturase, a Δ17 desaturase (e.g., *Saprolegnia diclina* Δ17 desaturase), a Δ4 desaturase and/or a C20 elongase. For example, a Δ15 desaturases may be *Aspergillus nidulans* Δ15 desaturase, the *Fusarium moniliforme* Δ12/Δ15 desaturase, the *Arabidopsis thaliana* Δ15 desaturase or the *M. alpina* Δ15 desaturase. In certain embodiments, a Δ6 desaturase may be an omega-6 specific Δ6 desaturase (e.g., *T. suecica* Δ6 desaturase, or *M. alpina* Δ6 desaturase) or an omega-3 specific Δ6 desaturase (e.g., *Primula juliae* Δ6 desaturase). Some examples of Δ9 elongases include, but are not limited to, *Euglena gracilis* Δ9 elongase and the *Isochrysis galbana* Δ9 elongase. In some embodiments, a Δ8 desaturase may be a *Tetruepretia pomquetensis* Δ8 desaturase or the *Euglena gracilis* Δ8 desaturase. In still a further embodiment, the additional fatty acid elongase or desaturase is operably linked to a seed-enhanced promoter.

In yet a further aspect, the invention provides a method for increasing EPA in a host cell or plant. In one embodiment, a method for increasing EPA content comprises expressing in the host cell or plant a Δ5 desaturase according to the invention and a Δ6 desaturase (e.g., an omega-3 specific Δ6 desaturase). In a further embodiments, a method for increasing EPA content further involves expressing a Δ15 desaturase in a host cell or plant. In another embodiment, a method for increasing EPA content in a plant comprises expressing in the host cell or plant a Δ5 desaturase according to the invention, a Δ9 elongase, a Δ8 desaturase and either a Δ15 desaturase or a Δ17 desaturase.

In still yet another aspect, the invention provides a method of producing a commercial product such as a food or feed, comprising the steps of (a) obtaining the transgenic plant of the invention; and (b) producing the commercial product from the tissue, seed, fruit and/or oil of that transgenic plant. For example, the commercial product may be a food or feed composition such as oil, silage, meal, grain, starch, flour or protein. The food or feed composition is defined as comprising a detectable polynucleotide sequence or detectable polypeptide provided by the invention. Additionally, the invention provides animal feed and human food compositions comprising EPA, ARA or DHA (see FIG. 4).

In still yet another aspect, the invention provides a method of increasing the nutritional value of an edible product for human or animal consumption, comprising adding transformed plants or plant parts, or derivatives thereof provided by the invention to the edible product. In certain embodiments, the product is human and/or animal food. The edible product may also be animal feed and/or a food supplement.

In still yet another aspect, the invention provides a method of manufacturing food or feed, comprising adding transformed plants or plant parts, or derivatives thereof provided by the invention to starting food or feed ingredients to produce the food or feed. In certain embodiments, the method is further defined as a method of manufacturing food and/or feed. The invention also provides food or feed made by the method.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

Figure 1:
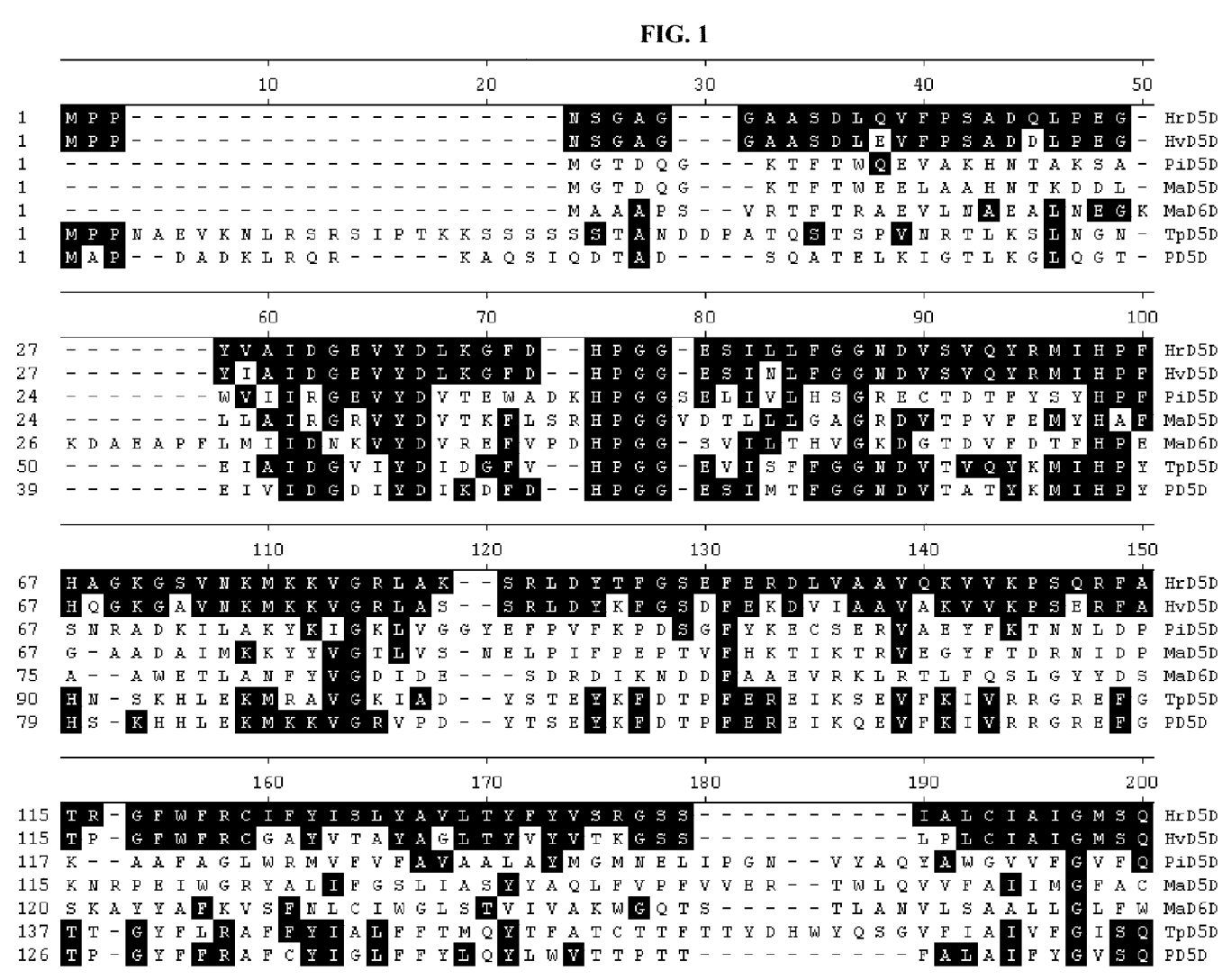
Figure 1:
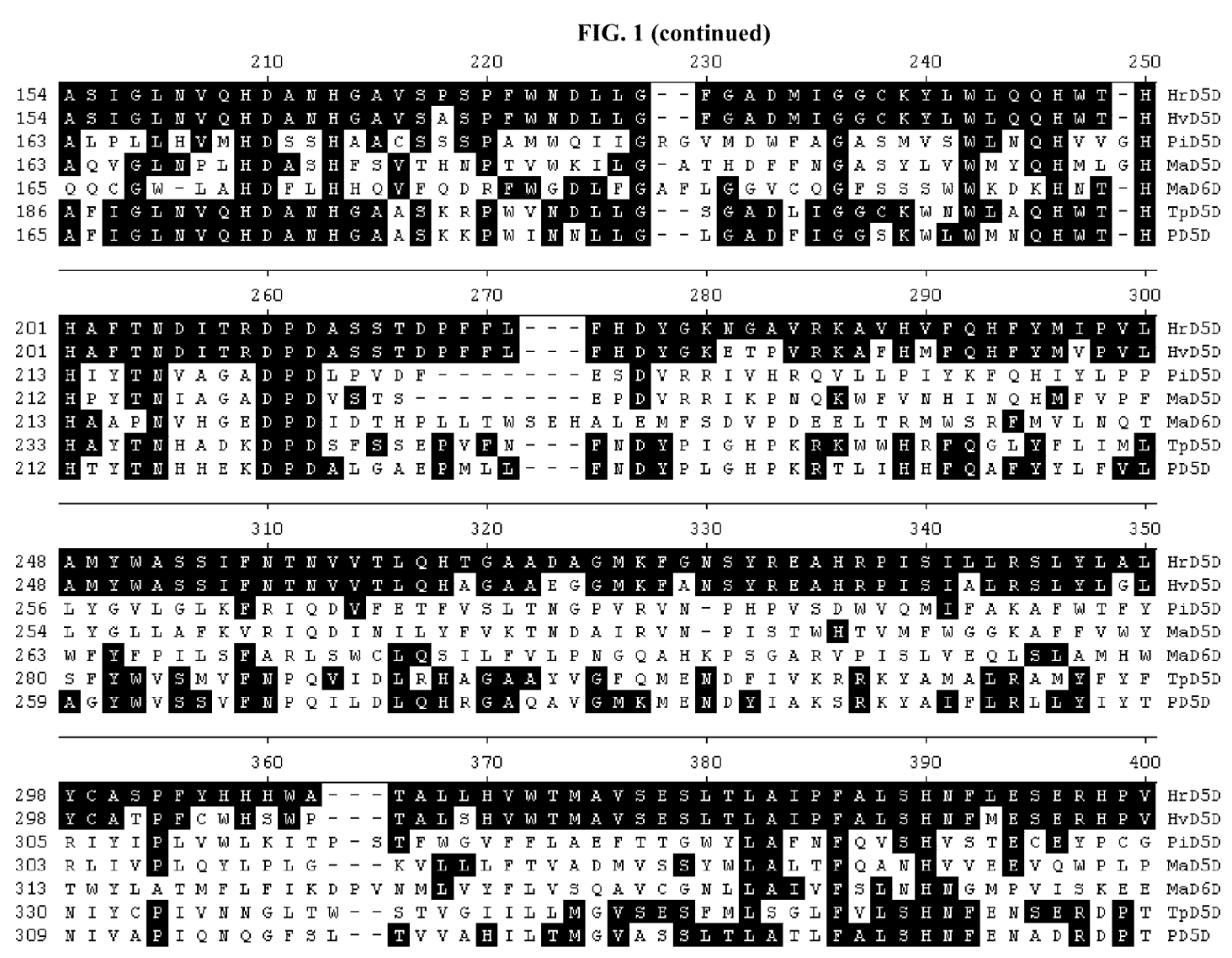
Figure 1:
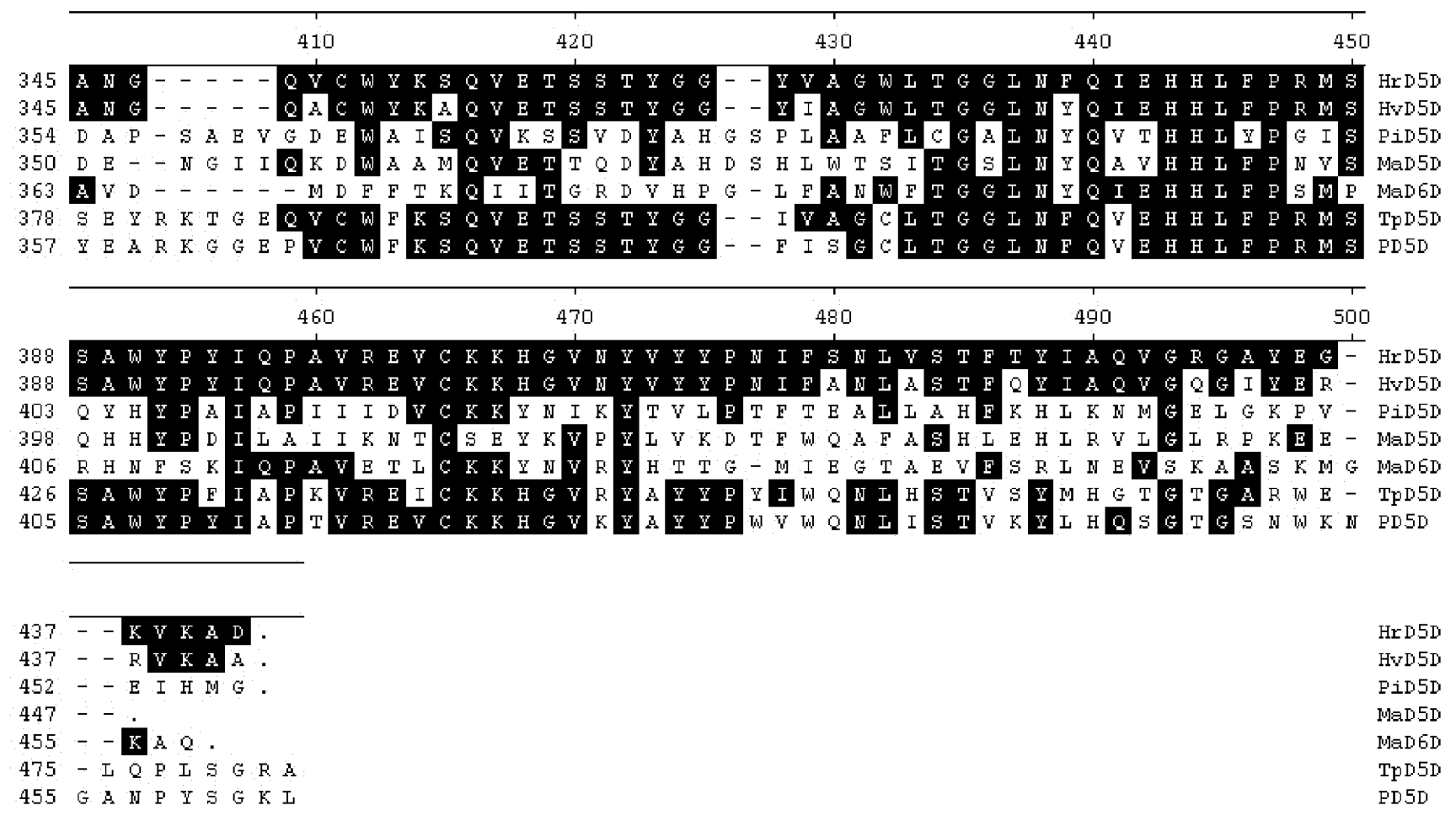

FIG. 1 illustrates an amino acid alignment of Δ5 desaturases from *Hemiselmis rufescens* HrD5D (SEQ ID NO: 4), *Hemiselmis virescens* HvD5D (SEQ ID NO: 2), *Pythium irregulare* PiD5D (SEQ ID NO: 10), *Mortierella alpina* D5D (SEQ ID NO: 11), *Thalassiosira pseudonana* TpD5D (SEQ ID NO: 13), *Peridinium* sp. CCMP626 PDSD (SEQ ID NO: 14), and the Δ6 desaturase from *Mortierella alpina* D6D (SEQ ID NO: 12).

DETAILED DESCRIPTION OF THE INVENTION

Figure 2:
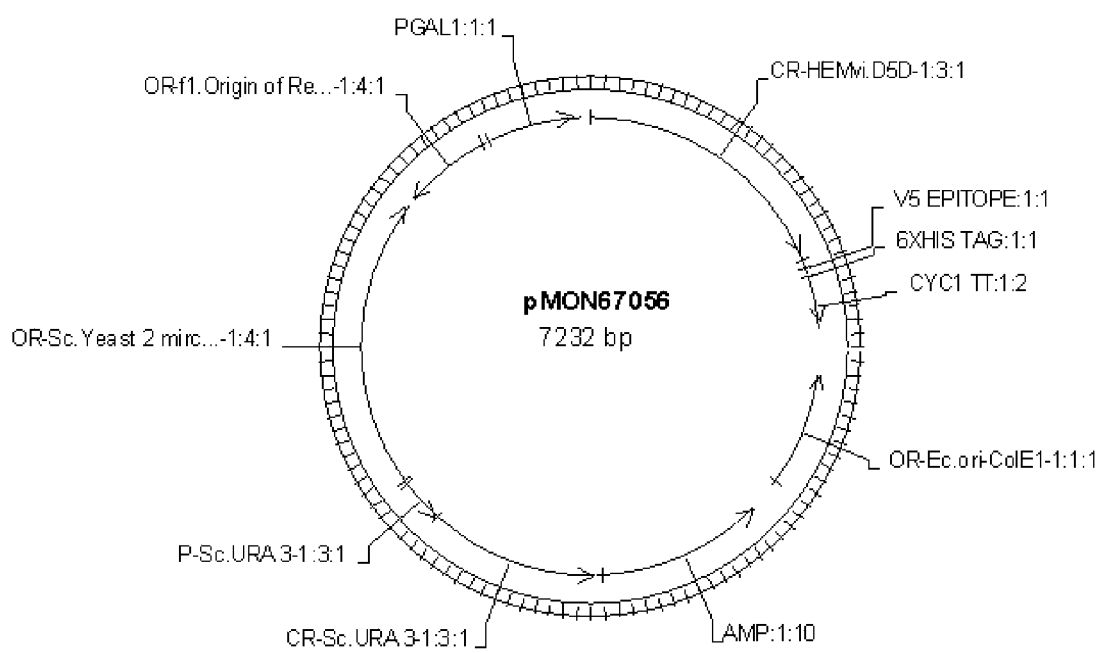
FIG. 2 illustrates a map of plasmid vector pMON67056.

The invention overcomes the limitations of the prior art by providing methods and compositions for creation of plants with enhanced PUFA content. The modification of fatty acid content of an organism such as a plant presents many advantages, including improved nutrition and health benefits for human and/or animal consumption. Modification of fatty acid content can be used to achieve beneficial levels or profiles of desired PUFA's in plants, plant parts, and plant products, including plant seed oils. For example, when the desired PUFA's are produced in the seed tissue of a plant, the oil may be isolated from the seeds typically resulting in an oil high in desired PUFAs or an oil having a desired fatty acid content or profile, which may in turn be used to provide beneficial characteristics in food stuffs and other products.

Various aspects of the invention include methods and compositions for modification of PUFA content of a cell, for example, modification of the PUFA content of a plant cell(s). Compositions related to the invention include novel isolated polynucleotide sequences, polynucleotide constructs and plants and/or plant parts transformed by polynucleotides of the invention. According to the current invention the isolated polynucleotide may encode a *Hemiselmis* ssp. Δ5 desaturase. Host cells may be manipulated to express a polynucleotide encoding a delta 5 desaturase polypeptide(s) which catalyze(s) desaturation of a fatty acid(s).

The following definitions are provided as an aid to understanding this invention. The phrases "DNA sequence," "nucleic acid sequence," "nucleic acid molecule," "polynucleotide" and "nucleic acid segment" refer to a physical structure comprising an orderly arrangement of nucleotides. The DNA segment, sequence, or nucleotide sequence may be contained within a larger nucleotide molecule, vector, or the like. In addition, the orderly arrangement of nucleic acids in these sequences may be depicted in the form of a sequence listing, figure, table, electronic medium, or the like.

The phrases "coding sequence," "coding region," "structural sequence," and "structural nucleic acid sequence" refer to all or a segment of a DNA sequence, nucleic acid sequence, nucleic acid molecule in which the nucleotides are arranged in a series of triplets that each form a codon. Each codon encodes a specific amino acid. Thus, the coding sequence, coding region, structural sequence, and structural nucleic acid sequence encode a series of amino acids forming a protein, polypeptide, motif or peptide sequence. The coding sequence, coding region, structural sequence, and structural nucleic acid sequence may be contained within a larger nucleic acid molecule, vector, or the like. In addition, the arrangement of nucleotides in these sequences may be depicted in the form of a sequence listing, figure, table, electronic medium, or the like.

The term "cDNA" refers to a double-stranded DNA that is complementary to and derived from mRNA.

"Desaturase" refers to a polypeptide that can desaturate or catalyze formation of a double bond between consecutive carbons of one or more fatty acids to produce a mono- or poly-unsaturated fatty acid or a precursor thereof. Of particular interest are polypeptides that can catalyze the conversion of DGLA to ARA or ETA to EPA by desaturating at the $5^{th}$ carbon from the carboxyl end of a fatty acid. Considerations for choosing a specific polypeptide having desaturase activity include, but are not limited to, the pH optimum of the polypeptide, whether the polypeptide is a rate limiting enzyme or a component thereof, whether the desaturase used is essential for synthesis of a desired PUFA, and/or whether a co-factor is required by the polypeptide. The expressed polypeptide preferably has characteristics that are compatible with the biochemical environment of its location in the host cell. For example, the polypeptide may have to compete for substrate(s).

"Elongase" refers to a polypeptide which lengthens fatty acids by adding two carbon atoms to the fatty acid's carboxylic acid end. Considerations for choosing a specific polypeptide having elongase activity include, but are not limited to, the pH optimum of the polypeptide, whether the polypeptide is a rate limiting enzyme or a component thereof, whether the elongase used is essential for synthesis of a desired PUFA, and/or whether a co-factor is required by the polypeptide. The expressed polypeptide preferably has characteristics that are compatible with the biochemical environment of its location in the host cell. For example, the polypeptide may have to compete for substrate(s "Expression" refers to the process by which a gene's coded information is converted into structures present and operating in the cell. Expressed genes include those that are transcribed into RNA and then translated into protein and those that are transcribed into RNA but not translated into protein (e.g., transfer RNA and ribosomal RNA).

As used herein, "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous" gene refers to a native gene in its natural location in the genome of an organism. An "exogenous" gene or "transgene" refer to a gene that has been introduced into the genome by a transformation procedure. A transgene includes genomic DNA introduced by a transformation procedure (e.g., a genomic DNA linked to its active promoter).

"Heterologous" refers to the relationship between 2 or more nucleic acid or protein sequences that are derived from different sources. For example, a promoter is heterologous with respect to a coding sequence if such a combination is not normally found in nature. In addition, a particular nucleic acid sequence may be "heterologous" with respect to a cell or organism into which it is inserted if it does not naturally occur in that particular cell or organism.

"Sequence similarity" refers to the level of similarity between 2 or more nucleic acid or amino acid sequences in terms of percent of positional identity. The term "homology" is used to refer to the concept of similar functional properties among different nucleic acids or proteins, for instance, due to shared evolutionary origin.

"Hybridization" refers to the ability of a first strand of nucleic acid to join with a second strand via hydrogen bond base pairing when the nucleic acid strands have sufficient sequence complementarity. As used herein, a nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Thus two nucleic acid strands are said to have sufficient complementarity when they can hybridize to one another with sufficient stability to permit them to remain annealed to one another under appropriate conditions.

The term "hybridization" refers generally to the ability of nucleic acid molecules to join via complementary base strand pairing. Such hybridization may occur when nucleic acid molecules are contacted under appropriate conditions. "Specifically hybridizes" refers to the ability of two nucleic acid molecules to form an anti-parallel, double-stranded nucleic acid structure. A nucleic acid molecule is said to be the "complement" of another nucleic acid molecule if they exhibit "complete complementarity," i.e., each nucleotide in one molecule is complementary to its base pairing partner nucleotide in another molecule. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

"Hybridization stringency" refers to conditions for hydrogen bonding between nucleic acid molecules. "Highly stringent" conditions tolerate little mismatch between a nucleic acid and a target strand. Such conditions are well known to those of ordinary skill in the art, and are preferred for applications requiring high selectivity. Medium stringent conditions may comprise relatively low salt and/or relatively high temperature conditions, such as provided by about 1×SSC, and 65° C. High stringency may for instance be defined as 0.02M to 0.10M NaCl and 50° C. to 70° C.; 5×SSC, 50% formamide and 42° C.; or 0.2×SSC and 65° C. Specific examples of such conditions include 0.02M NaCl and 50° C.; 0.02M NaCl and 60° C.; and 0.02M NaCl and 70° C. Nucleic acid molecules that hybridize to other nucleic acid molecules, e.g., at least under low stringency conditions are said to be "hybridizable cognates" of the other nucleic acid molecules. Conventional low stringency and high stringency conditions are described herein and by Sambrook et al., (*Molecular Cloning: A Laboratory Manual* $2^{nd}$ Ed., Cold Spring Harbor Laboratory Press, 1989) herein referred to as Sambrook et al., 1989, and by Haymes et al., 1985). Departures from complete complementarity are permissible, as long as such departures do not completely preclude the capacity of the molecules to form a double-stranded structure.

Low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989). High stringency conditions typically involve nucleic acid hybridization in about 2× to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) Ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. Hybridization is generally followed by several wash steps. The wash compositions generally comprise 0.5× to about 10×SSC, and 0.01% (w/v) to about 0.5% (w/v) SDS with a 15 minute incubation at about 20° C. to about 70° C. Preferably, the nucleic acid segments remain hybridized after washing at least one time in 0.1×SSC at 65° C.

The phrase "isolated" means having been removed from its natural environment, regardless of its eventual disposition. For example, a nucleic acid sequence "isolated" from rice, such as by cloning from a rice cell, remains "isolated" when it is inserted into the genome of a corn cell.

The phrase "operably linked" refers to the spatial arrangement of two or more nucleic acid regions or nucleic acid sequences so that they exert their appropriate effects with respect to each other. For example, a promoter region may be positioned relative to a nucleic acid sequence such that transcription of the nucleic acid sequence is directed by the promoter region. The promoter region and the nucleic acid sequence are "operably linked."

"Upstream" and "downstream" are positional terms used with reference to the location of a nucleotide sequence and the direction of transcription or translation of coding sequences, which normally proceeds in the 5' to 3' direction.

The terms "promoter" or "promoter region" refer to a nucleic acid sequence, usually found upstream (5') to a coding sequence, capable of directing transcription of a nucleic acid sequence into an RNA molecule. The promoter or promoter region typically provides a recognition site for RNA polymerase and the other factors necessary for proper initiation of transcription. As contemplated herein, a promoter or promoter region includes variations of promoters derived by inserting or deleting regulatory regions, subjecting the promoter to random or site-directed mutagenesis, and the like. The activity or strength of a promoter may be measured in terms of the amounts of RNA it produces, or the amount of protein accumulation in a cell or tissue, relative to a second promoter that is similarly measured.

The phrase "3' non-coding sequences" refers to nucleotide sequences located downstream of a coding sequence and include polyadenylation recognition sequences and other sequences encoding regulatory signals capable of affecting mRNA processing or gene expression. These are commonly referred to as 3'-untranslated regions or 3'-UTRs. The polyadenylation signal is usually characterized by affecting the addition of polyadenylic acid tracts to the 3' end of the mRNA precursor. The use of different 3' non-coding sequences is exemplified by Ingelbrecht et al. (1989).

"Translation leader sequence" or "5'-untranslated region" or "5'-UTR" all refer to a nucleotide sequence located between the promoter sequence of a gene and the coding sequence. The 5'-UTR is present in the fully processed mRNA upstream of the translation start sequence. The 5'-UTR may affect processing of the primary transcript to mRNA, mRNA stability or translation efficiency. Examples of translation leader sequences have been described (Turner and Foster, 1995).

"RNA transcript" refers to the product resulting from RNA polymerase-catalyzed transcription of a DNA sequence. When the RNA transcript is a perfect complementary copy of the DNA sequence, it is referred to as the primary transcript. An RNA sequence derived from posttranscriptional processing of the primary transcript is referred to as the mature RNA. "Messenger RNA" (mRNA) refers to the RNA that is without introns and that can be translated into polypeptide by the cell.

"DNA construct" refers to the heterologous genetic elements operably linked to each other making up a recombinant DNA molecule and may comprise elements that provide expression of a DNA polynucleotide molecule in a host cell and elements that provide maintenance of the construct. A plant expression cassette comprises the operable linkage of genetic elements that when transferred into a plant cell provides expression of a desirable gene product.

"Recombinant vector" refers to any agent by or in which a nucleic acid of interest is amplified, expressed, or stored, such as a plasmid, cosmid, virus, autonomously replicating sequence, phage, or linear single-stranded, circular single-stranded, linear double-stranded, or circular double-stranded DNA or RNA nucleotide sequence. The recombinant vector may be synthesized or derived from any source and is capable of genomic integration or autonomous replication.

"Regulatory sequence" refers to a nucleotide sequence located upstream (5'), within, or downstream (3') with respect to a coding sequence, or an intron, whose presence or absence affects transcription and expression of the coding sequence "Substantially homologous" refers to two sequences that are at least about 90% identical in sequence, as measured by the CLUSTAL W algorithm in, for example DNAStar (DNAStar, Madison, Wis.).

"Substantially purified" refers to a molecule separated from substantially all other molecules normally associated with it in its native state. More preferably, a substantially purified molecule is the predominant species present in a preparation. A substantially purified molecule may be greater than about 60% free, preferably about 75% free, more preferably about 90% free, and most preferably about 95% free from the other molecules (exclusive of solvent) present in the natural mixture. The phrase "substantially purified" is not intended to encompass molecules present in their native state. Preferably, the nucleic acid molecules and polypeptides of this invention are substantially purified.

The term "transformation" refers to the introduction of nucleic acid into a recipient host. The term "host" refers to bacteria cells, fungi, animals or animal cells, plants or seeds, or any plant parts or tissues including plant cells, protoplasts, calli, roots, tubers, seeds, stems, leaves, seedlings, embryos, and pollen.

As used herein, a "transgenic plant" is a plant having stably introduced into its genome, for example, the nuclear or plastid genomes, an exogenous nucleic acid.

The term "isogenic" as a comparative term between plants or plant lines having or lacking a transgene means plants or lines having the same or similar genetic backgrounds, with the exception of the transgene in question. For example, so-called sister lines representing phenotypically similar or identical selections from the same parent F2 population are considered to be "isogenic." When the progeny of a stable transformant plant are crossed and backcrossed with the plants of the untransformed parent line for 3 to 6 generations (or more) using the untransformed parent as the recurrent parent while selecting for type (genotype by molecular marker analysis, phenotype by field observation, or both) and for the transgene, the resulting transgenic line is considered to be highly "isogenic" to its untransformed parent line.

The terms "seeds" "kernels" and "grain" are understood to be equivalent in meaning. The term kernel is frequently used in describing the seed of a corn or rice plant. In all plants the seed is the mature ovule consisting of a seed coat, embryo, aleurone, and an endosperm.

Nucleic Acids Encoding Delta 5 Desaturases

The invention provides, in one embodiment, novel nucleic acids encoding delta 5 desaturases from *Hemiselmis* spp. In a particular embodiment, the nucleic acids are isolated from *Hemiselmis virescens*. strain CCMP442 and *Hemiselmis rufescens* strain CCMP439 (available from CCMP; Center for Culture of Marine Phytoplankton; West Boothbay Harbor, Me., USA). In certain embodiments, the nucleic acids comprise SEQ ID NOs:1 or 3. The invention also provides methods of using such nucleic acids, including SEQ ID NOs:1 and 3. In one embodiment, these nucleic acid molecules are used in the context of this invention for altering the oil composition of a seed from a plant.

Such nucleic acid can be amplified using cDNA, mRNA or genomic DNA as a template and appropriate oligonucleotide primers according to standard PCR™ amplification techniques. Alternatively, they can be synthesized using standard synthetic techniques, such as an automated DNA synthesizer. Polynucleotides encoding desired delta 5 desaturases can be identified in a variety of ways. As an example, a source of the desired delta 5 desaturases, for example a library from a *Hemiselmis* species, is screened with detectable enzymatically- or chemically-synthesized probes, which can be made from DNA, RNA, or non-naturally occurring nucleotides, or mixtures thereof. Probes may be enzymatically synthesized from polynucleotides of known delta 5 desaturases for normal or reduced-stringency hybridization methods. Oligonucleotide probes also can be used to screen sources and can be based on sequences of known delta 5 desaturases, including sequences conserved among known delta 5 desaturases, or on peptide sequences obtained from the desired purified protein. Oligonucleotide probes based on amino acid sequences can be degenerate to encompass the degeneracy of the genetic code, or can be biased in favor of the preferred codons of the source organism. Oligonucleotides also can be used as primers for PCR™ from reverse transcribed mRNA from a known or suspected source; the PCR™ product can be the full length cDNA or can be used to generate a probe to obtain the desired full length cDNA. Alternatively, a desired protein can be entirely sequenced and total synthesis of a DNA encoding that polypeptide performed.

Once the desired genomic or cDNA has been isolated, it can be sequenced by known methods. It is recognized in the art that such methods are subject to errors, such that multiple sequencing of the same region is routine and is still expected to lead to measurable rates of mistakes in the resulting deduced sequence, particularly in regions having repeated domains, extensive secondary structure, or unusual base compositions, such as regions with high GC base content. When discrepancies arise, resequencing can be done and can employ special methods. Special methods can include altering sequencing conditions by using: different temperatures; different enzymes; proteins which alter the ability of oligonucleotides to form higher order structures; altered nucleotides such as ITP or methylated dGTP; different gel compositions, for example adding formamide; different primers or primers located at different distances from the problem region; or different templates such as single stranded DNAs. Sequencing of mRNA also can be employed.

If desired, the sequences of nucleic acids that code for delta 5 desaturases can be modified without changing the resulting amino acid sequence of the expressed protein so that the sequences are more amenable to expression in plant hosts or other host cells. A coding sequence can be an artificial DNA. An artificial DNA, as used herein means a DNA polynucleotide molecule that is non-naturally occurring. Artificial DNA molecules can be designed by a variety of methods, such as, methods known in the art that are based upon substituting the codon(s) of a first polynucleotide to create an equivalent, or even an improved, second-generation artificial polynucleotide, where this new artificial polynucleotide is useful for enhanced expression in transgenic plants. The design aspect often employs a codon usage table produced by compiling the frequency of occurrence of codons in a collection of coding sequences isolated from a plant, plant type, family or genus. Other design aspects include reducing the occurrence of polyadenylation signals, intron splice sites, or long AT or GC stretches of sequence (U.S. Pat. No. 5,500,365). Full length coding sequences or fragments thereof can be made of artificial DNA using methods known to those skilled in the art. Modifications of the nucleotide sequences or regulatory elements disclosed herein which maintain the functions contemplated herein are within the scope of this invention. Such modifications include insertions, substitutions and deletions, and specifically substitutions which reflect the degeneracy of the genetic code.

The inventors have isolated DNA sequences from *Hemiselmis* spp that produce polypeptides with delta 5 desaturase activity. The sequences encoding the delta 5 desaturases may be expressed in transgenic plants, microorganisms or animals to modify fatty acid content. Other polynucleotides which are substantially identical to the delta 5 desaturase polynucleotides provided herein, or which encode polypeptides which are substantially identical to the delta 5 desaturase polypeptides, also can be used. "Substantially identical" refers to an amino acid sequence or nucleic acid sequence exhibiting in order of increasing preference at least 75%, 80%, 82%, 85%, 87%, 90%, 92%, 95%, 98 or 99% identity to the delta 5 desaturase polypeptide sequence in SEQ ID NO:2, SEQ ID NO:4 or sequences encoding these polypeptides. Polypeptide or polynucleotide comparisons may be carried out using sequence analysis software, for example, the Sequence Analysis software package of the GCG Wisconsin Package (Accelrys, San Diego, Calif.) and MEGAlign (DNAStar, Inc., 1228 S. Park St., Madison, Wis. 53715). Such software matches similar sequences by assigning degrees of similarity or identity.

DNA Constructs

The invention provides DNA constructs comprising a heterologous promoter operably linked to a nucleic acid described herein. The selection of promoters, e.g., promoters that may be described as strongly expressed, weakly expressed, inducibly expressed, tissue-enhanced expressed (i.e., specifically or preferentially expressed in a tissue), organ-enhanced expressed (i.e., specifically or preferentially expressed in an organ) and developmentally-enhanced expressed (i.e., specifically or preferentially expressed during a particular stage(s) of development), is within the skill in the art. Similarly, the combining of a nucleic acid molecule as described above with a promoter is also within the skill in the art (see, e.g., Sambrook et al., 2001).

Promoters for use with the invention include, but are not limited to, promoters that function in bacteria, bacteriophages, fungi or plant cells. Useful promoters for bacterial expression are the lacZ, Sp6, T7, T5 or *E. coli* glgC promoters. Useful promoters for fungi include *Saccharomyces cerevisiae* gal1 (West et al., 1984), *Saccharomyces pombe* nmt1 (Maundrell, 1990), *Neurospora crassa* ccg-1 (Freitag and Selker, 2005) and *Pichia methanolica* AUG1 (Invitrogen). Useful promoters for plants cells include the gamma zein Z27 promoter (see, for example, Prem Das et al., 1991), L3 oleosin promoter (U.S. Pat. No. 6,433,252, Kriz et al.), barley PER1 promoter (Stacey et al., 1996), CaMV 35S promoter (U.S. Pat. No. 5,530,196 (Fraley et al.)), nos promoter (Ebert et al., 1987), rice actin promoter (U.S. Pat. No. 5,641,876), and PEPCase promoter (Hudspeth et al., 1989). The Figwort Mosaic Virus (FMV) promoter (U.S. Pat. No. 6,051,753 (Comai et al.)), arcelin, tomato E8, patatin, ubiquitin, mannopine synthase (mas) and tubulin promoters are other examples of useful promoters.

There are a wide variety of plant promoter sequences which may be used to drive tissue-specific expression of polynucleotides encoding delta 5 desaturases and other desaturases in transgenic plants. Indeed, in particular embodiments of the invention, the promoter used is a seed-enhanced promoter. Examples of such promoters include the 5' regulatory regions from such genes as napin (Kridl et al., 1991), phaseolin (Bustos et al., 1989), soybean a' subunit of β-conglycinin (P-Gm7S alpha', see for example, Chen et al., 1986), *Vicia faba* USP (P-Vf.Usp, see for example, SEQ ID NOs:1, 2, and 3 of U.S. Patent Publication 20030229918), the globulin promoter (see for example Belanger and Kriz, 1991), and soybean alpha subunit of β-conglycinin (7S alpha) (U.S. Patent Publication 20030093828, incorporated by reference).

Other seed-expression enhanced promoters known to function in maize and in other plants include the promoters for the following genes: Waxy (granule bound starch synthase), Brittle and Shrunken 2 (ADP glucose pyrophosphorylase), Shrunken 1 (sucrose synthase), branching enzymes I and II, starch synthases, debranching enzymes, oleosins, glutelins, and Bet11 (basal endosperm transfer layer). Other promoters useful in the practice of the invention that are known by one of skill in the art are also contemplated by the invention.

Moreover, transcription enhancers or duplications of enhancers can be used to increase expression from a particular promoter. Examples of such enhancers include, but are not limited to the Adh intron1 (Callis et al., 1987), a rice actin intron (McElroy et al., 1991, U.S. Pat. No. 5,641,876), sucrose synthase intron (Vasil et al., 1989), a maize HSP70 intron (also referred to as Zm.DnaK) (U.S. Pat. No. 5,424,412, Brown et al.) a TMV omega element (Gallie et al., 1999), the CaMV 35S enhancer (U.S. Pat. Nos. 5,359,142 & 5,196,525, McPherson et al.) or an octopine synthase enhancer (U.S. Pat. No. 5,290,924, Last et al.). As the DNA sequence between the transcription initiation site and the start of the coding sequence, i.e. the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, 1987). The choice of such sequences is at the discretion of those of skill in the art.

DNA constructs of the invention may include a sequence near the 3' end of the cassette that acts as a signal to terminate transcription from a heterologous nucleic acid and that directs polyadenylation of the resultant mRNA. These are commonly referred to as 3' untranslated regions or 3' UTRs. Some 3' elements that can act as transcription termination signals include those from the nopaline synthase gene (nos) of *Agrobacterium tumefaciens* (Bevan et al., 1983), a napin 3' untranslated region (Kridl et al., 1991), a globulin 3' untranslated region (Belanger and Kriz, 1991), 3' untranslated region from the Adr12 gene of soybean (auxin down regulated) (Wang et al., PCT Publication WO200250295) or one from a zein gene, such as Z27 (Lopes et al., 1995). Other 3' regulatory elements known to the art also can be used in the vectors of the invention.

A nucleic acid molecule as described herein can be cloned into any suitable vector and can be used to transform or transfect any suitable host. The selection of vectors and methods to construct them are commonly known to the art and are described in general technical references (see, in general, Recombinant DNA Part D; *Meth. Enzymol.* 153:1-622, 1987). The vector will preferably comprise regulatory sequences, such as transcription and translation initiation and termination codons, which are specific to the type of host (e.g., bacterium, fungus, or plant) into which the vector is to be introduced, as appropriate and taking into consideration whether the vector is DNA or RNA.

Vectors that are circular or linear can be prepared to contain an entire nucleic acid sequence as described above or a portion thereof ligated to a replication system functional in a prokaryotic or eukaryotic host cell. Replication systems can be derived from ColE1, 2 mμ plasmid, λ phage, f1 filamentous phage, *Agrobacterium* species (e.g., *A. tumefaciens* and *A. rhizogenes*), and the like.

In addition to the replication system and the inserted nucleic acid sequence, the vector can include one or more marker genes that allow for selection of transformed or transfected hosts. Marker genes include biocide resistance, such as resistance to antibiotics, heavy metals, herbicides, etc., complementation in an auxotrophic host to provide prototrophy, and the like.

The invention provides host cells comprising a nucleic acid molecule described herein, optionally in the form of a vector. Suitable hosts include plant, bacterial and fungal cells, including *Escherichia coli, Bacillus subtilis, Agrobacterium tumefaciens, Saccharomyces cerevisiae* and *Neurospora crassa. E. coli* hosts include TB-1, TG-2, DH5α, XL-Blue MRF' (Stratagene, Austin, Tex.), SA2821, Y1090 and TG02. Plant cells include, but not limited to, soybean, *Brassica campestris*, canola, oilseed rape, rapeseed, crambe, mustard, castor bean, peanut, sesame, cottonseed, linseed, safflower, oil palm, flax, sunflower, alfalfa, corn, wheat, barley, oats, rye, millet, sorghum, and rice.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, integration of constructs can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

Expression in a host cell may involve fermentation techniques known to one skilled in the art. The fermented host cell may be a prokaryote, such as *Escherichia coli*, or a eukaryote, such as the yeast *Saccharomyces cerevisiae* or *Neurospora crassa*, a filamentous fungi. Examples of production of PUFA by fermentation include *Mortierella* (U.S. Pat. No. 6,319, 698) and *Thraustochytriales* (U.S. Pat. No. 6,451,567).

It is contemplated that more than one gene may be introduced and propagated in a host cell through the use of episomal or integrated expression vectors. Where two or more genes are expressed from separate replicating vectors, it is desirable that each vector has a different means of replication. Each introduced construct, whether integrated or not, should have a different means of selection and should lack homology to the other constructs to maintain stable expression and prevent reassortment of elements among constructs. Judicious choices of regulatory regions, selection means and method of propagation of the introduced construct can be experimentally determined so that all introduced polynucleotides are expressed at the necessary levels to provide for synthesis of the desired products.

Polypeptides

The invention provides delta 5 desaturases encoded by nucleic acid molecules described herein. Delta 5 desaturases are enzymes that can desaturate or catalyze formation of a double bond between consecutive carbons at the 5 position of one or more fatty acids to produce a mono- or poly-unsaturated fatty acid or a precursor thereof. The polypeptide can comprise D-amino acids, L-amino acids or a mixture of D- and L-amino acids.

Alterations of the native amino acid sequence to produce variant polypeptides can be prepared by a variety of means known to those ordinarily skilled in the art. For instance, amino acid substitutions can be conveniently introduced into the polypeptides by changing the sequence of the nucleic acid molecule at the time of synthesis. Site-specific mutations can also be introduced by ligating into an expression vector a synthesized oligonucleotide comprising the modified sequence. Alternately, oligonucleotide-directed, site-specific mutagenesis procedures can be used, such as disclosed in Walder et al. (1986); Bauer et al. (1985); and U.S. Pat. Nos. 4,518,584 and 4,737,462.

It is within the skill of the ordinary artisan to select synthetic and naturally-occurring amino acids that effect conservative or neutral substitutions for any particular naturally-occurring amino acids. The ordinarily skilled artisan desirably will consider the context in which any particular amino acid substitution is made, in addition to considering the hydrophobicity or polarity of the side-chain, the general size of the side chain and the pK value of side-chains with acidic or basic character under physiological conditions. For example, lysine, arginine, and histidine are often suitably substituted for each other, and more often arginine and histidine. As is known in the art, this is because all three amino acids have basic side chains, whereas the pK value for the side-chains of lysine and arginine are much closer to each other (about 10 and 12) than to histidine (about 6). Similarly, glycine, alanine, valine, leucine, and isoleucine are often suitably substituted for each other, with the proviso that glycine is frequently not suitably substituted for the other members of the group. This is because each of these amino acids is relatively hydrophobic when incorporated into a polypeptide, but glycines lack of an α-carbon allows the phi and psi angles of rotation (around the α-carbon) so much conformational freedom that glycinyl residues can trigger changes in conformation or secondary structure that do not often occur when the other amino acids are substituted for each other. Other groups of amino acids frequently suitably substituted for each other include, but are not limited to, the group consisting of glutamic and aspartic acids; the group consisting of phenylalanine, tyrosine and tryptophan; and the group consisting of serine, threonine and, optionally, tyrosine. Additionally, the ordinarily skilled artisan can readily group synthetic amino acids with naturally-occurring amino acids.

If desired, the polypeptides can be modified, for instance, by glycosylation, amidation, carboxylation, or phosphorylation, or by the creation of acid addition salts, amides, esters, in particular C-terminal esters, and N-acyl derivatives of the polypeptides of the invention. The polypeptides also can be modified to create protein derivatives by forming covalent or noncovalent complexes with other moieties in accordance with methods known in the art. Covalently-bound complexes can be prepared by linking the chemical moieties to functional groups on the side chains of amino acids comprising the polypeptides, or at the N- or C-terminus Desirably, such modifications and conjugations do not adversely affect the activity of the polypeptides (and variants thereof). While such modifications and conjugations can have greater or lesser activity, the activity desirably is not negated and is characteristic of the unaltered polypeptide.

The polypeptides (and fragments, variants and fusion proteins) can be prepared by any of a number of conventional techniques. The polypeptide can be isolated or substantially purified from a naturally occurring source or from a recombinant source. For instance, in the case of recombinant proteins, a DNA fragment encoding a desired protein can be subcloned into an appropriate vector using well-known molecular genetic techniques (see, e.g., Maniatis et al., 1989 and other references cited herein under "EXAMPLES"). The fragment can be transcribed and the protein subsequently translated in vitro. Commercially available kits also can be employed (e.g., such as manufactured by Clontech, Mountain View, Calif.; Amersham Life Sciences, Inc., Arlington Heights, Ill.; Invitrogen, Carlsbad, Calif. and the like). The polymerase chain reaction optionally can be employed in the manipulation of nucleic acids.

Polypeptides can be synthesized using an automated peptide synthesizer in accordance with methods known in the art. Alternately, the polypeptide (and fragments, variants, and fusion proteins) can be synthesized using standard peptide synthesizing techniques well-known to those of ordinary skill in the art (e.g., as summarized in Bodanszky, 1984). In particular, the polypeptide can be synthesized using the procedure of solid-phase synthesis (see, e.g., Merrifield, 1963; Barany et al., 1987 and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the protein from the resin can be accomplished by, for example, acid treatment at reduced temperature. The polypeptide-containing mixture then can be extracted, for instance, with diethyl ether, to remove non-peptidic organic compounds, and the synthesized protein can be extracted from the resin powder (e.g., with about 25% w/v acetic acid). Following the synthesis of the polypeptide, further purification (e.g., using HPLC) optionally can be done in order to eliminate any incomplete proteins, polypeptides, peptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation, or through genetic means known to the art. In this regard, this invention also provides a fusion protein comprising the polypeptide (or fragment thereof) or variant thereof and one or more other polypeptides/protein(s) having any desired properties or effector functions.

Assays for the production and identification of specific proteins are based on various physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches can be used to achieve even greater specificity such as western blotting in which antibodies are used to locate individual gene products that have been separated by electrophoretic techniques. Additional techniques can be used to absolutely confirm the identity of the product of interest such as evaluation by amino acid sequencing following purification. Although these are among the most common, other procedures can also be used.

Assay procedures can identify the expression of proteins by their functionality, particularly where the expressed protein is an enzyme capable of catalyzing chemical reactions involving specific substrates and products. For example, in plant extracts these reactions can be measured by providing and quantifying the loss of substrates or the generation of products of the reactions by physical and/or chemical procedures.

In many cases, the expression of a gene product is determined by evaluating the phenotypic results of its expression. Such evaluations may be simply as visual observations, or may involve assays. Such assays can take many forms, such as analyzing changes in the chemical composition, morphology, or physiological properties of the plant. Chemical composition may be altered by expression of genes encoding enzymes or storage proteins that change amino acid composition and these changes can be detected by amino acid analysis, or by enzymes that change starch quantity, which can be analyzed by near infrared reflectance spectrometry or by enzymes that change oil composition, which can be detected by gas chromatography. Morphological changes may include greater stature or thicker stalks.

The nucleic acid molecules, DNA constructs and polypeptides of this invention can be used in agricultural methods and various screening assays. For example, a nucleic acid molecule can be used to express a delta 5 desaturase via a vector in a host cell, to detect mRNA transcripts encoding delta 5 desaturases in a biological sample, to detect a genetic alteration in a gene encoding delta 5 desaturase via a Southern blot, to suppress delta 5 desaturases, or to up-regulate delta 5 desaturases. The polypeptides can be used to compensate for deficiencies in delta 5 desaturases or for the presence of a mutated delta 5 desaturases having reduced or no activity in a plant, or to treat excessive levels of substrates, whether direct or indirect, for delta 5 desaturases in a plant. Alternatively, the polypeptides can be used to screen agents for the ability to modulate their activity. The antibodies can be used to detect and isolate the respective polypeptides as well as decrease the availability of such polypeptides in vivo.

Plant Transformation

In a preferred embodiment of the invention, a transgenic plant expressing the desired protein or proteins is produced. Various methods for the introduction of a desired polynucleotide sequence encoding the desired protein into plant cells are known to the art, including: (1) physical methods such as microinjection, electroporation, and microparticle-mediated delivery (biolistics or gene gun technology); (2) virus-mediated delivery; or (3) Rhizobia-mediated, such as *Agrobacterium*-mediated, transformation.

The most commonly used methods for transformation of plant cells are the *Agrobacterium*-mediated DNA transfer process and the biolistics or microprojectile microparticle bombardment mediated process. Typically, nuclear transformation is desired but where it is desirable to specifically transform plastids, such as chloroplasts or amyloplasts, plant plastids may be transformed utilizing a microparticle-mediated delivery of the desired polynucleotide.

An *Agrobacterium*-mediated transformation is achieved through the use of a genetically engineered soil bacterium belonging to the genus *Agrobacterium*. A number of wild-type and disarmed strains of *Agrobacterium tumefaciens* and *Agrobacterium rhizogenes* harboring Ti or Ri plasmids can be used for gene transfer into plants. Gene transfer is done via the transfer of a specific DNA known as "T-DNA" that can be genetically engineered to carry any desired piece of DNA into many plant species, as further elaborated, for example, in U.S. Pat. No. 6,265,638 to Bidney et al., the disclosures of which are hereby incorporated herein by reference.

An *Agrobacterium*-mediated genetic transformation of plants involves several steps. The first step, in which the virulent *Agrobacterium* and plant cells are first brought into contact with each other, is generally called "inoculation". Inoculation is preferably accompanied by some method of injury to some of the plant cells, which releases plant cellular constituents, such as coumaryl alcohol, sinapinate (which is reduced to acetosyringone), sinapyl alcohol and coniferyl alcohol, that activate virulence factors in the *Agrobacterium*. Following the inoculation, the *Agrobacterium* and plant cells/tissues are permitted to grow together for a period of several hours to several days or more under conditions suitable for growth and T-DNA transfer. This step is termed "co-culture". Following co-culture and T-DNA delivery, the plant cells are treated with bactericidal or bacteriostatic agents to kill the *Agrobacterium* remaining in contact with the explant and/or in the vessel containing the explant. If this is done in the absence of any selective agents to promote preferential growth of transgenic versus non-transgenic plant cells, then this is typically referred to as the "delay" step. If done in the presence of selective pressure favoring transgenic plant cells, then it is referred to as a "selection" step. When a "delay" is used, it is typically followed by one or more "selection" steps.

With respect to microparticle bombardment (U.S. Pat. No. 5,550,318 (Adams et al.); U.S. Pat. No. 5,538,880 (Lundquist et. al.), U.S. Pat. No. 5,610,042 (Chang et al.); and PCT WO 95/06128 (Adams et al.); each of which is specifically incorporated herein by reference in its entirety), microscopic particles are coated with nucleic acids and delivered into cells by a propelling force. Exemplary particles include those comprised of tungsten, platinum, and preferably, gold.

An illustrative embodiment of a method for delivering DNA into plant cells by acceleration is the Biolistics® Particle Delivery System (BioRad, Hercules, Calif.), which can be used to propel particles coated with DNA or cells through a screen, such as a stainless steel or NYTEX screen, onto a filter surface covered with monocot plant cells cultured in suspension.

Microparticle bombardment techniques are widely applicable, and may be used to transform virtually any plant species. Examples of species that have been transformed by microparticle bombardment include monocot species such as maize (International Publication No. WO 95/06128 (Adams et al.)), barley, wheat (U.S. Pat. No. 5,563,055 (Townsend et al.)) incorporated herein by reference in its entirety), rice, oat, rye, sugarcane, and sorghum; as well as a number of dicots including tobacco, soybean (U.S. Pat. No. 5,322,783 (Tomes et al.)), incorporated herein by reference in its entirety), sunflower, peanut, cotton, tomato, and legumes in general (U.S. Pat. No. 5,563,055 (Townsend et al.)) incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scoreable marker would include but are not limited to β-glucuronidase (GUS), green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline. Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. No. 5,627,061 (Barry, et al.), U.S. Pat. No. 5,633,435 (Barry, et al.), and U.S. Pat. No. 6,040,497 (Spencer, et al.) and aroA described in U.S. Pat. No. 5,094,945 (Comai) for glyphosate tolerance; a polynucleotide molecule encoding bromoxynil nitrilase (Bxn) described in U.S. Pat. No. 4,810,648 (Duerrschnabel, et al.) for Bromoxynil tolerance; a polynucleotide molecule encoding phytoene desaturase (crtI) described in Misawa et al. (1993); Misawa et al. (1994) for norflurazon tolerance; a polynucleotide molecule encoding acetohydroxyacid synthase (AHAS, aka ALS) described in Sathasiivan et al. (1990) for tolerance to sulfonylurea herbicides; and both the pat gene described in Wohlleben et al., (1988) and bar gene described in DeBlock et al. (1987), each of which provides glufosinate and bialaphos tolerance.

The regeneration, development, and cultivation of plants from various transformed explants are well documented in the art. This regeneration and growth process typically includes the steps of selecting transformed cells and culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. Developing plantlets are transferred to soil less plant growth mix, and hardened off, prior to transfer to a greenhouse or growth chamber for maturation.

This invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves. The Tomes et al. '783 patent, cited above, describes a method of treatment with a cytokinin followed by incubation for a period sufficient to permit undifferentiated cells in cotyledonary node tissue to differentiate into meristematic cells and to permit the cells to enter the phases between the G1 and division phases of development, which is stated to improve susceptibility for transformation.

According to the current invention, any suitable plant culture medium can be used. Suitable media include but are not limited to MS-based media (Murashige and Skoog, 1962) or N6-based media (Chu et al., 1975) supplemented with additional plant growth regulators including but not limited to auxins, cytokinins, ABA, and gibberellins. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Those of skill in the art are aware that media and media supplements such as nutrients and growth regulators for use in transformation and regeneration and other culture conditions such as light intensity during incubation, pH, and incubation temperatures that can be optimized for the particular variety of interest.

After a DNA construct is stably incorporated in transgenic plants and confirmed to be operable, it can be introduced into other plants of the same or another sexually compatible species by sexual crossing. Any of a number of standard breeding techniques can be used, depending upon the species to be crossed. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes or alleles relative to a starting plant line, as disclosed herein, is defined as the techniques that result in a particular sequence being introduced into a plant line by crossing a starting line with a donor plant line that comprises a transgene or allele of the invention. To achieve this one could, for example, perform the following steps: (a) plant seeds of the first (starting line) and second (donor plant line that comprises a desired transgene or allele) parent plants; (b) grow the seeds of the first and second parent plants into plants that bear flowers; (c) pollinate a flower from the first parent plant with pollen from the second parent plant; and (d) harvest seeds produced on the parent plant bearing the fertilized flower.

Backcrossing is herein defined as the process including the steps of: (a) crossing a plant of a first genotype containing a desired gene, DNA sequence or element to a plant of a second genotype lacking said desired gene, DNA sequence or element; (b) selecting one or more progeny plant containing the desired gene, DNA sequence or element; (c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

Seeds, Meal, Oil and Products Comprising Seeds, Meal and Oil

This invention also provides a container of over about 1000, more preferably about 20,000, and even more preferably about 40,000 seeds where over about 10%, more preferably about 25%, more preferably about 50%, and even more preferably about 75% or more preferably about 90% of the seeds are seeds derived from a plant of this invention.

This invention also provides a container of over about 10 kg, more preferably about 25 kg, and even more preferably about 50 kg seeds where over about 10%, more preferably about 25%, more preferably about 50%, and even more preferably about 75% or more preferably about 90% of the seeds are seeds derived from a plant of this invention.

Any of the plants or parts thereof of this invention may be harvested and, optionally, processed to produce a feed, meal, or oil preparation. A particularly preferred plant part for this purpose is harvested seed, but other plant parts can be harvested and used for stover or silage. Methods to produce feed, meal, and oil preparations are known in the art. See, for example, U.S. Pat. Nos. 4,957,748; 5,100,679; 5,219,596; 5,936,069; 6,005,076; 6,146,669; and 6,156,227. The grain or meal of this invention may be blended with other grains or meals.

Methods

The present invention provides a method for providing transgenic plants with an increased content of EPA or ARA. This method may include, for example, introducing DNA encoding a delta 5 desaturase and optionally at least one additional desaturase into plant cells and regenerating plants with increased EPA or ARA content from the transgenic cells.

More specifically, the invention provides a method of producing food or feed, comprising the steps of (a) obtaining the transgenic plant of the invention; and (b) producing the food or feed. The food or feed may be oil, silage, meal, grain, starch, flour or protein. The food or feed composition is defined as comprising a detectable polynucleotide sequence or detectable polypeptide provided by the invention. Additionally, the invention provides animal feed and human food compositions comprising EPA or ARA.

For dietary supplementation, the purified PUFAs, transformed plants or plant parts, or derivatives thereof, may be incorporated into cooking oils, fats or margarines formulated so that in normal use the recipient would receive the desired amount. The PUFAs may also be incorporated into infant formulas, nutritional supplements or other food products, and may find use as anti-inflammatory or cholesterol lowering agents.

As used herein, "edible composition" is defined as compositions which may be ingested by a mammal such as foodstuffs, nutritional substances and pharmaceutical compositions. As used herein "foodstuffs" refer to substances that can be used or prepared for use as food for a mammal and include substances that may be used in the preparation of food (such as frying oils) or food additives. For example, foodstuffs include animals used for human consumption or any product there from, such as, for example, eggs. Typical foodstuffs include but are not limited to beverages, (e.g., soft drinks, carbonated beverages, ready to mix beverages), infant formula, infused foods (e.g., fruits and vegetables), sauces, condiments, salad dressings, fruit juices, syrups, desserts (e.g., puddings, gelatin, icings and fillings, baked goods and frozen desserts such as ice creams and sherbets), soft frozen products (e.g., soft frozen creams, soft frozen ice creams and yogurts, soft frozen toppings such as dairy or non-dairy whipped toppings), oils and emulsified products (e.g., shortening, margarine, mayonnaise, butter, cooking oil, and salad dressings) and intermediate moisture foods (e.g., rice and dog foods).

Furthermore, edible compositions described herein can also be ingested as an additive or supplement contained in foods and drinks. These can be formulated together with a nutritional substance such as various vitamins and minerals and incorporated into substantially liquid compositions such as nutrient drinks, soymilks and soups; substantially solid compositions; and gelatins or used in the form of a powder to be incorporated into various foods. The content of the effective ingredient in such a functional or health food can be similar to the dose contained in a typical pharmaceutical agent.

The purified PUFAs, transformed plants or plant parts may also be incorporated into animal, particularly livestock, feed. In this way, the animals themselves may benefit from a PUFA rich diet, while human consumers of food products produced from such livestock may benefit as well.

For pharmaceutical use (human or veterinary), the compositions may generally be administered orally but can be administered by any route by which they may be successfully absorbed, e.g., parenterally (i.e., subcutaneously, intramuscularly or intravenously), rectally, vaginally or topically, for example, as a skin ointment or lotion. The PUFAs, transformed plants or plant parts of the present invention may be administered alone or in combination with a pharmaceutically acceptable carrier or excipient. Where available, gelatin capsules are the preferred form of oral administration. Dietary supplementation as set forth above can also provide an oral route of administration. The unsaturated acids of the present invention may be administered in conjugated forms, or as salts, esters, amides or prodrugs of the fatty acids. Any pharmaceutically acceptable salt is encompassed by the present invention; especially preferred are the sodium, potassium or lithium salts. Also encompassed are the N-alkylpolyhydroxamine salts, such as N-methyl glucamine, found in PCT publication WO 96/33155. The preferred esters are the ethyl esters. As solid salts, the PUFAs also can be administered in tablet form. For intravenous administration, the PUFAs or derivatives thereof may be incorporated into commercial formulations such as Intralipids (Pharmacia—Upjohn, Peapack, N.J.).

EXAMPLES

The following examples are included to illustrate embodiments of the invention. It should be appreciated by those of skill in the art that the techniques disclosed in the examples that follow represent techniques discovered by the inventor to function well in the practice of the invention. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Cloning of *Hemiselmis* Δ5 Desaturase Sequences

The Δ5 desaturases of the current invention were cloned from *Hemiselmis virescens* and *Hemiselmis rufescens*. To clone the *Hemiselmis virescens* Δ5 desaturase (HvD5D), RNA was isolated from *H. virescens* CCMP442 (CCMP, West Boothbay Harbor, Me., USA) followed by the construction of a cDNA library. Approximately 20,000 independent clones were sequenced. Searching for desaturase-related sequences yielded a putative Δ5 desaturase-encoding clone, LIB5446-048-A1-M1-G2.

The DNA sequence of the cloned insert for LIB5446-048-A1-M1-G2 (SEQ ID NO: 5) was 1613 bp in length and contained an open reading frame (ORF) of 1326 bp (SEQ ID NO: 1), encoding a deduced amino acid sequence of 441 amino acids (SEQ ID NO: 2). The calculated size of the protein is 48.9 Kdal with an estimated pI of 7.1. The ORF, referred to as HvD5D, contained the conserved amino acid sequence HPGG (SEQ ID NO: 24), which is part of the cytochrome b5 (cytb5) domain fused to the N-terminus of front-end desaturases. All characterized front-end desaturases, including Δ4-, Δ5-, Δ6-, and Δ8-desaturases have this N-terminal cytb5 domain. In addition, the deduced amino acid sequence of LIB5446-048-A1-M1-G2 has three conserved histidine boxes; most notably a QXXHH (SEQ ID NO: 25) sequence, which is found at the third histidine box and is also diagnostic of front-end desaturases (Napier et al., 1997, Napier et al., 2003, Sperling and Heinz, 2001). The three conserved histidine boxes are part of the active site and are thought to be required to bind a diiron cofactor required for activity.

The 1326 bp region containing the putative Δ5 desaturase coding region from LIB5446-048-A1-M1-G2 was amplified by PCR and ligated into the yeast expression vector pYES2.1-TOPO (Invitrogen, Carlsbad Calif.), giving pMON67056 (FIG. 2). The primers used for amplification are shown below:

```
Hv D5 M1G2 F1:
5'-GTCGACAAACAATGCCTCCCAACAGTGGCG-3' (SEQ ID NO: 6)

Hv D5 M1G2 R1:
5'-CCTGCAGGTCAGGCCGCCTTGACCCTC-3'   (SEQ ID NO: 7)
```

A SalI restriction site and a Kozak sequence were added to the 5' end of the Hv D5 M1G2 F1 oligonucleotide and an Sse8387I restriction site was added to the 5' end of the Hv D5 M1G2 R1 oligonucleotide.

To clone the *Hemiselmis rufescens* Δ5 desaturase (HrD5D), RNA was isolated from *H. rufescens* CCMP439 (CCMP, West Boothbay Harbor, Me., USA) followed by the construction of a cDNA library. An EST library consisting of ~23,790 clones was screened for sequences that contained consensus front-end desaturases as described above. A partial clone was identified, LIB5445-223-A1-M1-D4, that contained all of the previously described conserved sequences except for the cytb5 region (HPGG). A 5' RACE reaction was utilized to complete the ORF of this putative front-end desaturase, which was subsequently ligated into pYES2.1/

Figure 3:
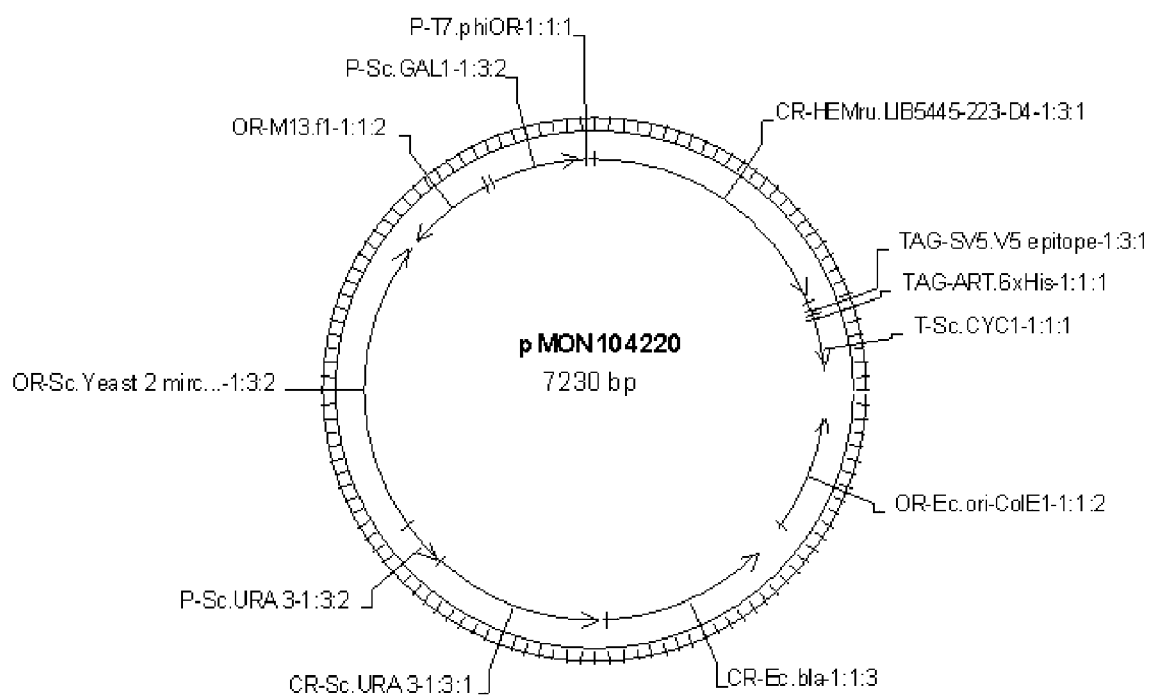
FIG. 3 illustrates a map of plasmid vector pMON104220.
Figure 4:
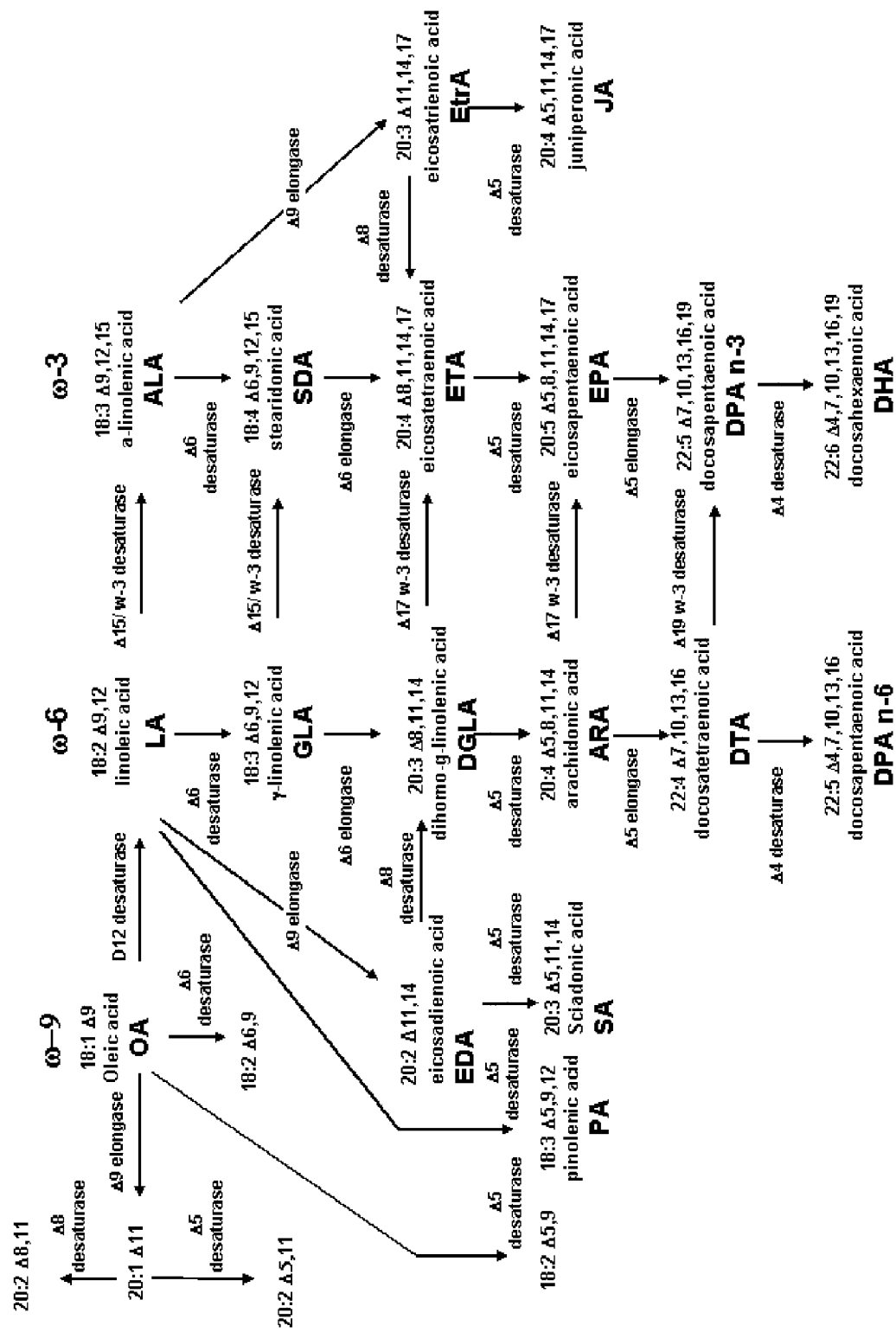
FIG. 4 illustrates a pathway diagram for PUFA biosynthesis.

V5-His-TOPO® (Invitrogen, Carlsbad, Calif.) to give pMON104220 (FIG. 3). The primers used to PCR amplify the full-length ORF were:

(SEQ ID NO: 8)
H.ruf223
5'-CAGTCGACAAACAATGCCCCCCAACAGCGGCGCGGGAG-3'
and, (SEQ ID NO: 9)
3'revH.Ruf223
5'-CACCTGCAGGTCAGTCGGCTTTGACCTTCCCTTCG-3'.

The ORF for this clone was 1323 bp (SEQ ID NO: 3; not including the stop codon) encoding a deduced amino acid sequence of 441 amino acids (SEQ ID NO: 4). This protein has an estimated size of 49 Kdal and a pI of 8.2.

A pairwise alignment of the 45 desaturases from *Hemiselmis rufescens*, *Hemiselmis virescens*, *Pythium irregulare*, *Mortierella alpina*, *Thalassiosira pseudonana* and *Peridinium* sp. CCMP626 as well as a Δ6 desaturase from *Mortierella alpina* is shown in Table 1. The two *Hemiselmis* Δ5 desaturases are the most similar showing 86.9% identity. By comparison, the identities to two other Δ5 desaturases from phytoplankton, *Thalassiosira pseudonana* and *Peridinium* sp. CCMP626 ranged from 48.5% to 50.9%. The *Hemiselmis* Δ5 desaturases share even less identity to the Δ5 desaturases from a water mold, *P. irregulare* (Oomycetes), and an oleaginous fungus, *M. alpina*, with ranges from 21.9% to 23.4%. The highest levels of homology are found in the areas around the two histidine boxes, the Q box, and the conserved HPGG box of the cytb5 domain (FIG. 1).

TABLE 1

Pair-wise alignment percentage identities for deduced amino acid sequences of Δ5 and Δ6 desaturases.

| 1 | 2 | 3 | 4 | 5 | 6 | 7 | Organism |
|---|---|---|---|---|---|---|---|
| — | 86.9 | 22.9 | 21.9 | 23 | 49.2 | 50.9 | *Hemiselmis rufescens* Δ5 SEQ ID NO: 4 |
|   | — | 23.4 | 23.3 | 23.7 | 48.5 | 50.7 | *Hemiselmis virescens* Δ5 SEQ ID NO: 2 |
|   |   | — | 39.6 | 20.4 | 22.9 | 23.6 | *Pythium irregulare* Δ5 SEQ ID NO: 10 |
|   |   |   | — | 20.4 | 23.6 | 23.1 | *Mortierella alpina* Δ5 SEQ ID NO: 11 |
|   |   |   |   | — | 21.7 | 21.1 | *Mortierella alpina* Δ6 SEQ ID NO: 12 |
|   |   |   |   |   | — | 65.9 | *Thalassiosira pseudonana* Δ5 SEQ ID NO: 13 |
|   |   |   |   |   |   | — | *Peridinium* sp. CCMP626 Δ5 SEQ ID NO: 14 |

*P. irregulare* Δ5 desaturase (GenBank Accession AAL13311).
*M. alpina* Δ5 desaturase (Accession AAC72755).
*M. alpina* Δ6 desaturase (Accession AAF08685).
*T. pseudonana* Δ5 desaturase (Accession DJ418329).
*Peridinium* sp CCMP626 Δ5 desaturase (US20070271632, SEQ ID NO: 2 thereof).

Example 2

Yeast Transformation and Expression

The pYES2.1/V5-His-TOPO® clones containing HvD5D and HrD5D were introduced into the host strain *Saccharomyces cerevisiae* INVSc1 (auxotrophic for uracil) (Invitrogen) using the S.C. EasyComp™ Transformation Kit (Invitrogen). Transformants were selected on plates made of SC minimal media minus uracil with 2% glucose. Colonies of transformants were used to inoculate 2 ml of SC minimal media minus uracil and 2% glucose grown overnight at 30° C. For induction, stationary phase yeast cells were pelleted and re-suspended at 0.4 O.D. $A_{600}$ in SC minimal media minus uracil supplemented with 2% galactose and optional exogenous fatty acids and grown for 3 days at 15° C. When exogenous fatty acids were provide to the cultures, either 0.01% DGLA (18:2 Δ8, 11, 14) or 0.01% ETA (20:4 Δ8, 11, 14, 17) was added with 0.1% of the emulsifier Tergitol. The cultures were harvested by centrifugation after 3 days of incubation with these fatty acids. Cell pellets were washed once with sterile TE buffer pH 7.5, to remove the media, and lyophilized to dryness. The host strain transformed with the empty vector pYES2/CT was used as a negative control in all experiments.

Lipids were extracted from lyophilized yeast pellets by adding 0.1 mL toluene and incubating over-night at room temperature. Extracted lipids were converted to fatty acid methyl esters (FAMEs) in situ by addition of 0.5 mL 0.6N sodium methoxide in methanol and incubating for 45 min at room temperature. The FAMEs were extracted by addition of 0.8 mL 10% (w/v) NaCl and 0.15 mL of heptane. After vigorous shaking followed by phase separation, the heptane layer containing FAMEs was removed and used directly for gas chromatography (GC). The FAMEs were identified on a Hewlett-Packard 5890 II Plus GC (Hewlett-Packard, Palo Alto, Calif.) equipped with a flame-ionization detector and a capillary column (Omegawax 250™; 30 m×0.25 mm i.d.× 0.25 μm; Supelco, Bellefonte, Pa.). The injector was maintained at 250° C. and the flame ionization detector was maintained at 270° C. The column temperature was maintained at 180° C. for 1.5 min following injection, increased to 240° C. at 40° C./min, and held at 245° C. for 3.38 min.

The results shown in Table 2 demonstrate that *Hemiselmis* clones HvD5D and HrD5D exhibit Δ5 desaturase activity in a yeast expression system. The enzyme activity was deduced from a yeast induction assay, whereby yeast cultures induced to express recombinant desaturase are fed DGLA or ETA. The yeast incorporates these fatty acids into their membranes where they become substrates for the recombinant desaturase. The products of DGLA and ETA desaturation are ARA (20:4 Δ5, 8, 11, 14) and EPA (20:5 Δ5, 8, 11, 14, 17), respectively. Two individual yeast colonies were selected for each vector and grown in triplicate. Values are shown as the average of 6 assays. Both *Hemiselmis* clones demonstrated enzymatic activity with ETA and DGLA.

TABLE 2

Delta 5 desaturase activity of *Hemiselmis* spp. HvD5D and HrD5D in a yeast expression system.

| Construct | Fatty Acid in Medium | DGLA | ETA | AA | EPA | % Conv |
|---|---|---|---|---|---|---|
| HvD5D | ETA | 0.0 | 6.5 | 0.0 | 3.7 | 36.2 |
| HrD5D | ETA | 0.0 | 6.0 | 0.0 | 4.7 | 44.1 |
| Negative control | ETA | 0.0 | 10.2 | 0.0 | 0.0 | 0.0 |
| HvD5D | DGLA | 5.2 | 0.0 | 2.5 | 0.0 | 32.7 |
| HrD5D | DGLA | 5.4 | 0.0 | 3.2 | 0.0 | 37.8 |
| Negative control | DGLA | 7.2 | 0.0 | 0.0 | 0.0 | 0.0 |

Example 3

Expression of the *Hemiselmis* Spp. Δ5 Desaturases in Soybean and Canola

The activity of the *Hemiselmis virescens* or the *Hemiselmis rufescens* Δ5 desaturase is evaluated in soybean by expressing it under the control of seed-enhanced promoter in a soybean background that contains expression cassettes for other fatty acid desaturases which produce the dihomo-γ-linolenic acid (DGLA) and/or eicosatetraenoic acid (ETA) substrate fatty acid molecules that the Δ5 desaturase transforms into arachidonic acid (ARA) or eicosapentaenoic acid (EPA), respectively. Seed-enhanced expression of transgenes in plants in general and in soybean specifically is well established in the art. Using standard molecular cloning techniques the gene of interest is cloned either as wild-type sequence or as a sequence codon-enhanced for expression for the plant of interest downstream of a seed-enhanced promoter. Examples for seed-enhanced promoters of dicotyledonous plants such as soybean or canola are the 7Sα promoter, 7Sα' promoter, Arcelin-5 promoter, napin promoter and oleosin promoter. In between the promoter sequence and the coding region of the gene of interest, a 5'-untranslated region (5'-UTR) is inserted to stabilize the mRNA. This sequence typically includes the transcriptional start site. Downstream of the translational stop codon, a 3'-untranslated region (3'-UTR) is added to stabilize the mRNA and to terminate transcription. In plants the ETA or DGLA substrates for either Δ5 desaturase can be generated via the Δ6 pathway or via the Δ8 pathway. To generate DGLA via the Δ6 pathway the plant background that is transformed with an expression cassette for the *H. virescens* or the *H. rufescens* Δ5 desaturase must contain seed-enhanced expression cassettes for a Δ6 desaturase, preferably an omega-6 specific Δ6 desaturase, such as the *T. suecica* Δ6 desaturase, or the *M. alpina* Δ6 desaturase and a Δ6 or C18 elongase, such as the *M. alpina* Δ6 elongase. For generation of ETA via the Δ6 pathway, the Δ6 desaturase expression cassette preferably contains a gene encoding an omega-3 preferring enzyme, such as the *Primula juliae* Δ6 desaturase. Additionally, the plant background preferably also contains a seed-enhanced expression cassette for a Δ15 desaturase, such as the *Aspergillus nidulans* Δ15 desaturase, the *Fusarium moniliforme* Δ12/Δ15 desaturase, the *Arabidopsis thaliana* Δ15 desaturase or the *M. alpina* Δ15 desaturase. The additional expression cassettes described as part of the plant background can be transformed separately and crossed in or combined with the gene of interest by re-transformation of selected lines, or they can be co-transformed with the gene of interest in a co-bombardment, in an *Agrobacterium* mediated co-transformation as part of multiple T-DNAs or in a transformation on a single DNA construct, e.g., via *Agrobacterium* mediated transformation. All of these methods are well established in the art.

To generate the DGLA or ETA substrates via the Δ8 pathways, the Δ5 desaturase expression constructs have to be transformed into a plant background that contains a seed-enhanced expression cassette for a Δ9 elongase such as the *Euglena gracilis* Δ9 elongase or the *Isochrysis galbana* Δ9 elongase as well as a seed-enhanced expression cassette for a Δ8 desaturase, such as the *Pavlova* sp. Δ8 desaturase, the *Tetruepretia pomquetensis* Δ8 desaturase or the *Euglena gracilis* Δ8 desaturase. To generate predominantly the ETA substrate via the Δ8 pathway, the plant background harboring the Δ9 elongase expression construct and the Δ8 desaturase expression construct also should contain a seed-enhanced expression construct for a Δ15 desaturase such as the *A. nidulans* Δ15 desaturase, the *F. moniliforme* Δ12/Δ15 desaturase, the *A. thaliana* Δ15 desaturase, or the *M. alpina* Δ15 desaturase. As an alternative to including the expression construct for the Δ15 desaturase, a seed-enhanced expression construct for a Δ17 desaturase, such as the *S. diclina* Δ17 desaturase, can be utilized. The latter pathway generates ETA predominantly via the DGLA intermediate, while the former pathway can be designed to generate ETA predominantly via the stearidonic acid (SDA) intermediate.

When the Δ5 desaturase is expressed in a plant background that produces the DGLA substrate via one of the pathways described above, ARA is generated. To generate EPA, DPA (n-3), or DHA, additional desaturases and elongases are required. The supplemental expression of an omega-3 desaturase such as a Δ17 desaturase, for example, a *Saprolegnia diclina* Δ17 desaturase expressed seed specifically converts DGLA to ETA and ARA to EPA.

To generate the DGLA substrate while keeping ETA levels low, expression of the cellular delta-15 desaturase can be reduced or completely suppressed by seed-enhanced expression of an RNAi construct while at the same time a C18 elongase is co-expressed with a delta-8 desaturase. In such a background seed-enhanced expression of a delta-5 desaturase results in the predominant formation of ARA.

Plant backgrounds that additionally contain a seed-enhanced expression cassette containing a C20 elongase, for example, the *Euglena gracilis* C20 elongase, or a C20 elongase and a Δ-4 desaturase expression construct accumulate DPA or DPA/DHA, respectively. An example of a Δ-4 desaturase of the invention is the *Schizochytrium aggregatum* Δ4 desaturase.

Strategies to express the *H. virescens* or the *H. rufescens* Δ5 desaturase in canola are identical to the strategies in soybean or other dicotyledonous plants.

Transformed dicotyledonous explants containing constructs as described above are obtained via *Agrobacterium tumefaciens*-mediated transformation. Plants are regenerated from transformed tissue. The greenhouse-grown plants are then analyzed for oil composition.

For example, the activity of the *H. virescens* or the *H. rufescens* Δ5 desaturase was determined in soy also transformed with other genes necessary for PUFA production. These cassettes included the *Neurospora crassa* Δ15 desaturase driven by the USP88 promoter, the *M. alpina* Δ6 desaturase driven by the 7Sα' promoter and the *M. alpina* Δ6 elongase driven by the 7Sα promoter. Plants containing the 3 cassettes described above will be referred to as the control. For comparison, the Δ5 desaturases from *Saprolegnia diclina* and *Isochrysis galbana* were also transformed into the same background. Each Δ5 desaturase was expressed under the control of the USP88 promoter. The transformed soy explants containing constructs as described above were obtained via *Agrobacterium tumefaciens*-mediated transformation. Plants were regenerated from transformed tissue. The greenhouse-grown plants were then analyzed for oil composition. Multiple transformation events are shown for each Δ5 desaturase and the control.

TABLE 3

Delta 5 desaturase activity of *Hemiselmis* spp. HvD5D and HrD5D in soy (Fatty acids 18:1 through 18:2).

| Element | Oleic | 18:2D5,9 | 18:2D6,9 |
|---|---|---|---|
| Control | 21.45 | 0.00 | 0.25 |
| Control | 25.30 | 0.05 | 0.56 |
| Control | 26.11 | 0.00 | 0.55 |
| Control | 17.06 | 0.00 | 0.32 |
| Control | 13.97 | 0.00 | 0.11 |
| Control | 16.69 | 0.00 | 0.18 |
| Control | 25.10 | 0.00 | 0.64 |
| Control | 16.01 | 0.00 | 0.17 |
| Control | 18.07 | 0.00 | 0.24 |
| Control | 16.85 | 0.00 | 0.16 |
| Control | 19.09 | 0.00 | 0.32 |

TABLE 3-continued

Delta 5 desaturase activity of *Hemiselmis* spp. HvD5D and HrD5D in soy (Fatty acids 18:1 through 18:2).

| Element | Oleic | 18:2D5,9 | 18:2D6,9 |
|---|---|---|---|
| Control | 16.02 | 0.01 | 0.15 |
| Control | 26.77 | 0.00 | 0.89 |
| Control | 18.59 | 0.00 | 0.23 |
| Control | 20.69 | 0.00 | 0.32 |
| Control | 33.35 | 0.00 | 1.26 |
| Control | 20.30 | 0.00 | 0.33 |
| Control | 18.75 | 0.00 | 0.30 |
| Control | 17.60 | 0.00 | 0.21 |
| Control | 18.66 | 0.01 | 0.30 |
| Control | 27.01 | 0.01 | 0.48 |
| Control | 18.84 | 0.00 | 0.37 |
| Control | 16.40 | 0.00 | 0.24 |
| HvD5d | 29.48 | 0.15 | 0.77 |
| HvD5d | 18.84 | 0.16 | 0.25 |
| HvD5d | 30.02 | 0.11 | 0.75 |
| HvD5d | 23.67 | 0.00 | 1.67 |
| HvD5d | 19.46 | 0.10 | 0.28 |
| HvD5d | 22.45 | 0.12 | 0.39 |
| HvD5d | 23.56 | 0.08 | 0.39 |
| HvD5d | 17.60 | 0.02 | 0.42 |
| HvD5d | 20.86 | 0.11 | 0.35 |
| HvD5d | 16.23 | 0.01 | 0.15 |
| HvD5d | 20.36 | 0.06 | 0.22 |
| HvD5d | 23.09 | 0.00 | 0.25 |
| HvD5d | 17.18 | 0.06 | 0.19 |
| HvD5d | 20.89 | 0.06 | 0.44 |
| HvD5d | 14.30 | 0.12 | 0.14 |
| HvD5d | 18.67 | 0.08 | 0.22 |
| HvD5d | 17.32 | 0.05 | 0.23 |
| HrD5D | 33.77 | 0.27 | 0.69 |
| HrD5D | 34.96 | 0.38 | 1.35 |
| HrD5D | 32.17 | 0.29 | 0.76 |
| HrD5D | 33.11 | 0.48 | 0.60 |
| HrD5D | 28.29 | 0.21 | 0.53 |
| HrD5D | 25.28 | 0.21 | 0.38 |
| HrD5D | 24.69 | 0.33 | 0.60 |
| HrD5D | 30.52 | 0.22 | 0.68 |
| HrD5D | 15.29 | 0.11 | 0.10 |
| HrD5D | 33.60 | 0.34 | 0.95 |
| HrD5D | 20.36 | 0.18 | 0.42 |
| HrD5D | 23.02 | 0.18 | 0.30 |
| HrD5D | 18.64 | 0.16 | 0.22 |
| HrD5D | 23.85 | 0.18 | 0.38 |
| HrD5D | 18.92 | 0.17 | 0.17 |
| HrD5D | 42.04 | 0.17 | 1.03 |
| HrD5D | 30.66 | 0.23 | 0.87 |
| HrD5D | 20.47 | 0.01 | 0.45 |
| HrD5D | 20.09 | 0.06 | 0.24 |
| HrD5D | 17.22 | 0.02 | 0.20 |
| HrD5D | 22.06 | 0.06 | 0.42 |
| HrD5D | 20.13 | 0.00 | 0.94 |
| SdD5D | 31.92 | 4.48 | 0.95 |
| SdD5D | 28.14 | 3.34 | 0.55 |
| SdD5D | 17.89 | 2.00 | 0.11 |
| SdD5D | 40.70 | 6.81 | 1.50 |
| SdD5D | 19.05 | 1.68 | 0.26 |
| SdD5D | 35.14 | 5.01 | 1.03 |
| SdD5D | 28.02 | 3.57 | 0.38 |
| SdD5D | 30.57 | 3.34 | 0.85 |
| SdD5D | 27.84 | 2.60 | 0.96 |
| SdD5D | 26.63 | 2.87 | 0.54 |
| SdD5D | 22.45 | 0.00 | 0.47 |
| SdD5D | 18.41 | 1.71 | 0.21 |
| SdD5D | 37.35 | 5.42 | 1.06 |
| SdD5D | 24.61 | 3.45 | 0.50 |
| SdD5D | 21.24 | 0.16 | 0.40 |
| SdD5D | 25.79 | 3.67 | 0.47 |
| SdD5D | 27.36 | 0.10 | 0.58 |
| SdD5D | 24.47 | 1.68 | 0.38 |
| SdD5D | 20.00 | 0.08 | 0.36 |
| SdD5D | 33.69 | 4.46 | 1.07 |
| SdD5D | 35.88 | 2.02 | 1.80 |
| SdD5D | 18.75 | 0.05 | 0.30 |
| SdD5D | 14.49 | 0.11 | 0.05 |
| SdD5D | 15.65 | 0.08 | 0.19 |
| SdD5D | 13.83 | 0.05 | 0.17 |
| IgD5D | 21.72 | 0.04 | 0.45 |
| IgD5D | 21.45 | 0.03 | 0.45 |
| IgD5D | 19.44 | 0.04 | 0.51 |
| IgD5D | 23.26 | 0.06 | 0.48 |
| IgD5D | 26.69 | 0.09 | 0.86 |
| IgD5D | 17.03 | 0.00 | 0.31 |
| IgD5D | 18.02 | 0.00 | 0.24 |
| IgD5D | 42.95 | 0.08 | 1.83 |
| IgD5D | 20.32 | 0.02 | 0.32 |
| IgD5D | 18.35 | 0.03 | 0.35 |
| IgD5D | 19.44 | 0.02 | 0.32 |
| IgD5D | 17.48 | 0.00 | 0.22 |
| IgD5D | 21.69 | 0.07 | 0.48 |
| IgD5D | 18.27 | 0.02 | 0.25 |
| IgD5D | 20.08 | 0.07 | 0.19 |
| IgD5D | 16.68 | 0.03 | 0.26 |
| IgD5D | 40.86 | 0.09 | 0.96 |
| IgD5D | 19.19 | 0.02 | 0.38 |

TABLE 4

Delta 5 desaturase activity of *Hemiselmis* spp. HvD5D and HrD5D in soy (Fatty acids 18:3 and greater).

| Element | LA | GLA | DGLA | EDA | AA | ALA | SDA | ETA | EtrA | JA | EPA | DPA |
|---|---|---|---|---|---|---|---|---|---|---|---|---|
| Control | 9.24 | 5.14 | 4.57 | 2.37 | 0.0 | 17.60 | 6.59 | 7.52 | 4.82 | 0.00 | 0.0 | 0.00 |
| Control | 6.79 | 6.19 | 3.76 | 1.23 | 0.0 | 16.21 | 8.67 | 6.81 | 3.29 | 0.00 | 0.0 | 0.00 |
| Control | 7.27 | 3.78 | 2.97 | 1.77 | 0.0 | 18.77 | 6.69 | 6.77 | 5.33 | 0.00 | 0.0 | 0.00 |
| Control | 9.56 | 8.43 | 4.50 | 1.26 | 0.0 | 20.41 | 10.58 | 6.47 | 2.80 | 0.00 | 0.0 | 0.00 |
| Control | 9.73 | 6.90 | 4.10 | 1.38 | 0.0 | 23.05 | 10.31 | 6.36 | 3.23 | 0.00 | 0.0 | 0.00 |
| Control | 10.48 | 8.10 | 4.02 | 1.33 | 0.0 | 21.11 | 10.16 | 5.81 | 2.88 | 0.01 | 0.0 | 0.00 |
| Control | 8.98 | 7.04 | 4.62 | 1.68 | 0.0 | 16.24 | 7.79 | 5.71 | 3.31 | 0.00 | 0.0 | 0.00 |
| Control | 9.15 | 7.59 | 3.57 | 1.12 | 0.0 | 22.65 | 12.01 | 5.47 | 2.79 | 0.00 | 0.0 | 0.00 |
| Control | 10.87 | 9.27 | 3.92 | 1.03 | 0.0 | 20.84 | 10.87 | 4.99 | 2.08 | 0.01 | 0.0 | 0.00 |
| Control | 9.82 | 7.66 | 3.01 | 0.99 | 0.0 | 23.38 | 10.94 | 4.98 | 2.47 | 0.00 | 0.0 | 0.00 |
| Control | 11.93 | 7.66 | 4.76 | 2.37 | 0.0 | 17.53 | 6.77 | 4.96 | 3.53 | 0.00 | 0.0 | 0.00 |
| Control | 8.66 | 7.54 | 2.64 | 1.01 | 0.0 | 23.90 | 12.48 | 4.86 | 2.80 | 0.00 | 0.0 | 0.00 |
| Control | 7.00 | 8.70 | 3.67 | 0.91 | 0.0 | 15.37 | 11.81 | 4.77 | 1.76 | 0.00 | 0.0 | 0.00 |
| Control | 10.24 | 8.92 | 3.26 | 1.23 | 0.0 | 20.37 | 10.61 | 4.33 | 2.58 | 0.00 | 0.0 | 0.00 |
| Control | 12.07 | 8.93 | 3.96 | 1.41 | 0.0 | 18.41 | 8.93 | 4.19 | 2.09 | 0.00 | 0.0 | 0.00 |
| Control | 8.90 | 8.42 | 3.20 | 0.77 | 0.0 | 13.80 | 8.65 | 4.02 | 1.59 | 0.01 | 0.0 | 0.00 |
| Control | 11.37 | 8.76 | 3.56 | 1.39 | 0.0 | 19.37 | 9.62 | 3.99 | 2.30 | 0.00 | 0.0 | 0.00 |

TABLE 4-continued

Delta 5 desaturase activity of *Hemiselmis* spp. HvD5D and HrD5D in soy
(Fatty acids 18:3 and greater).

| Element | LA | GLA | DGLA | EDA | AA | ALA | SDA | ETA | EtrA | JA | EPA | DPA |
|---|---|---|---|---|---|---|---|---|---|---|---|---|
| Control | 10.23 | 9.74 | 2.76 | 0.90 | 0.0 | 20.84 | 12.84 | 3.33 | 1.56 | 0.00 | 0.0 | 0.00 |
| Control | 14.17 | 9.61 | 3.16 | 1.29 | 0.0 | 20.73 | 9.03 | 3.20 | 1.91 | 0.00 | 0.0 | 0.00 |
| Control | 14.11 | 10.82 | 2.46 | 0.91 | 0.0 | 20.39 | 10.06 | 2.48 | 1.21 | 0.00 | 0.0 | 0.00 |
| Control | 10.11 | 10.60 | 0.02 | 0.00 | 0.0 | 19.95 | 15.42 | 0.02 | 0.01 | 0.00 | 0.0 | 0.00 |
| Control | 11.64 | 10.76 | 0.00 | 0.00 | 0.0 | 24.88 | 15.57 | 0.00 | 0.00 | 0.00 | 0.0 | 0.00 |
| Control | 11.43 | 11.89 | 0.00 | 0.00 | 0.0 | 25.18 | 17.02 | 0.00 | 0.00 | 0.00 | 0.0 | 0.00 |
| HvD5D | 5.71 | 5.01 | 2.83 | 1.40 | 0.0 | 15.03 | 7.34 | 4.07 | 3.20 | 1.42 | 3.4 | 1.29 |
| HvD5D | 10.52 | 5.56 | 3.00 | 2.52 | 1.3 | 19.41 | 6.31 | 2.75 | 3.82 | 1.64 | 2.6 | 0.04 |
| HvD5D | 7.51 | 6.45 | 3.53 | 1.70 | 1.1 | 14.56 | 7.00 | 2.94 | 2.39 | 0.90 | 2.2 | 0.04 |
| HvD5D | 9.53 | 8.39 | 2.66 | 1.05 | 0.9 | 16.56 | 10.11 | 2.49 | 1.43 | 0.51 | 2.2 | 0.97 |
| HvD5D | 12.25 | 8.54 | 2.96 | 1.98 | 1.1 | 19.02 | 7.64 | 2.14 | 2.23 | 1.03 | 1.8 | 0.00 |
| HvD5D | 11.28 | 8.47 | 2.49 | 1.51 | 0.9 | 18.19 | 9.43 | 1.96 | 1.87 | 0.95 | 1.8 | 0.00 |
| HvD5D | 12.14 | 8.61 | 2.66 | 1.54 | 0.3 | 17.67 | 8.73 | 1.92 | 1.50 | 0.90 | 1.8 | 0.10 |
| HvD5D | 14.85 | 8.32 | 3.06 | 2.04 | 1.3 | 19.43 | 6.83 | 1.86 | 1.90 | 0.78 | 1.7 | 0.00 |
| HvD5D | 12.14 | 8.17 | 2.36 | 1.92 | 0.9 | 18.60 | 8.52 | 1.76 | 2.26 | 1.11 | 1.7 | 0.00 |
| HvD5D | 13.54 | 9.42 | 2.11 | 1.16 | 0.8 | 22.28 | 10.22 | 1.68 | 1.36 | 0.83 | 1.6 | 0.68 |
| HvD5D | 14.32 | 9.81 | 2.44 | 1.16 | 0.0 | 19.88 | 9.11 | 1.56 | 1.11 | 0.50 | 1.2 | 0.06 |
| HvD5D | 12.80 | 10.49 | 1.25 | 0.67 | 0.5 | 20.34 | 10.80 | 0.97 | 0.82 | 0.45 | 0.9 | 0.07 |
| HvD5D | 15.29 | 10.28 | 1.76 | 1.04 | 0.6 | 21.88 | 10.44 | 1.01 | 0.91 | 0.39 | 0.9 | 0.21 |
| HvD5D | 15.57 | 11.80 | 0.89 | 0.65 | 0.3 | 20.09 | 10.62 | 0.56 | 0.58 | 0.24 | 0.5 | 0.22 |
| HvD5D | 17.79 | 8.54 | 6.97 | 4.27 | 0.1 | 14.59 | 5.59 | 3.82 | 3.11 | 0.02 | 0.2 | 0.01 |
| HvD5D | 15.67 | 12.64 | 0.02 | 0.13 | 0.0 | 23.43 | 13.04 | 0.01 | 0.02 | 0.00 | 0.0 | 0.00 |
| HvD5D | 14.16 | 12.37 | 0.02 | 0.03 | 0.0 | 24.59 | 14.39 | 0.02 | 0.01 | 0.00 | 0.0 | 0.00 |
| HrD5d | 4.69 | 4.60 | 2.79 | 1.39 | 1.2 | 12.39 | 6.24 | 3.24 | 2.53 | 1.64 | 3.1 | 0.00 |
| HrD5d | 4.00 | 5.65 | 2.45 | 0.90 | 1.1 | 10.63 | 8.15 | 3.03 | 1.51 | 1.41 | 3.0 | 1.06 |
| HrD5d | 6.37 | 6.68 | 2.39 | 1.18 | 1.0 | 13.37 | 8.42 | 2.28 | 1.53 | 1.28 | 2.3 | 0.20 |
| HrD5d | 9.02 | 6.23 | 3.15 | 1.86 | 1.4 | 12.87 | 5.69 | 2.05 | 1.47 | 1.37 | 2.1 | 0.15 |
| HrD5d | 9.63 | 8.07 | 2.87 | 1.14 | 1.0 | 15.84 | 8.25 | 2.26 | 1.19 | 0.92 | 2.0 | 0.15 |
| HrD5d | 10.62 | 8.29 | 3.12 | 1.48 | 1.2 | 15.86 | 7.66 | 2.15 | 1.44 | 1.12 | 2.0 | 0.00 |
| HrD5d | 9.85 | 7.65 | 2.95 | 2.01 | 1.4 | 15.98 | 7.75 | 1.92 | 1.81 | 1.55 | 2.0 | 0.00 |
| HrD5d | 8.17 | 8.05 | 2.84 | 1.19 | 1.1 | 13.95 | 8.91 | 2.14 | 1.12 | 0.96 | 1.9 | 0.65 |
| HrD5d | 13.13 | 7.86 | 2.55 | 1.90 | 1.2 | 21.98 | 8.66 | 1.80 | 2.10 | 1.46 | 1.9 | 0.66 |
| HrD5d | 6.22 | 7.49 | 2.40 | 0.96 | 1.0 | 13.28 | 9.74 | 1.96 | 1.01 | 0.96 | 1.9 | 0.64 |
| HrD5d | 11.08 | 8.29 | 2.90 | 1.71 | 1.2 | 18.65 | 8.55 | 2.01 | 1.81 | 1.31 | 1.9 | 0.00 |
| HrD5d | 12.24 | 8.35 | 2.58 | 1.35 | 1.0 | 18.18 | 8.00 | 1.83 | 1.43 | 1.02 | 1.8 | 0.00 |
| HrD5d | 11.39 | 8.38 | 2.22 | 1.20 | 0.9 | 21.05 | 10.50 | 1.83 | 1.42 | 1.03 | 1.7 | 0.02 |
| HrD5d | 10.67 | 8.89 | 2.48 | 1.19 | 0.9 | 17.80 | 9.64 | 1.69 | 1.18 | 0.87 | 1.6 | 0.00 |
| HrD5d | 13.14 | 9.44 | 2.75 | 1.73 | 1.2 | 18.87 | 8.66 | 1.58 | 1.54 | 1.11 | 1.5 | 0.23 |
| HrD5d | 7.49 | 5.37 | 1.61 | 1.25 | 0.8 | 11.21 | 5.31 | 1.24 | 1.39 | 0.73 | 1.5 | 0.00 |
| HrD5d | 8.82 | 8.59 | 1.90 | 0.95 | 0.7 | 15.75 | 9.98 | 1.40 | 1.02 | 0.64 | 1.2 | 1.07 |
| HrD5d | 8.67 | 5.32 | 2.90 | 2.06 | 0.0 | 17.32 | 9.66 | 6.49 | 4.21 | 0.00 | 0.8 | 0.22 |
| HrD5d | 9.67 | 6.29 | 4.11 | 2.49 | 0.1 | 19.35 | 7.47 | 4.78 | 4.53 | 0.01 | 0.6 | 0.50 |
| HrD5d | 12.15 | 10.89 | 0.23 | 0.16 | 0.1 | 25.44 | 15.22 | 0.21 | 0.21 | 0.19 | 0.2 | 0.19 |
| HrD5d | 10.99 | 12.81 | 0.01 | 0.02 | 0.0 | 21.15 | 16.46 | 0.01 | 0.01 | 0.00 | 0.0 | 0.49 |
| HrD5d | 10.80 | 12.61 | 0.00 | 0.00 | 0.0 | 22.06 | 17.22 | 0.00 | 0.00 | 0.00 | 0.0 | 0.29 |
| SdD5D | 6.60 | 5.43 | 1.78 | 1.17 | 0.6 | 13.68 | 7.32 | 2.02 | 1.99 | 1.19 | 1.5 | 0.23 |
| SdD5D | 12.21 | 8.00 | 2.23 | 0.42 | 0.8 | 17.20 | 7.45 | 1.89 | 0.42 | 0.26 | 1.4 | |
| SdD5D | 13.42 | 7.88 | 2.63 | 1.55 | 0.9 | 20.56 | 7.70 | 2.01 | 1.67 | 0.72 | 1.4 | |
| SdD5D | 4.78 | 4.22 | 1.82 | 0.96 | 0.7 | 9.45 | 4.95 | 1.46 | 1.11 | 0.94 | 1.3 | 0.21 |
| SdD5D | 13.80 | 8.38 | 1.97 | 1.26 | 0.8 | 21.02 | 7.40 | 1.74 | 1.77 | 0.81 | 1.3 | |
| SdD5D | 8.53 | 6.32 | 1.80 | 1.00 | 0.7 | 11.95 | 5.73 | 1.47 | 1.12 | 0.84 | 1.1 | 0.18 |
| SdD5D | 8.97 | 6.49 | 1.95 | 1.76 | 0.7 | 14.44 | 7.23 | 1.59 | 2.22 | 1.17 | 1.1 | 0.27 |
| SdD5D | 10.79 | 7.86 | 2.16 | 1.02 | 0.7 | 14.12 | 6.75 | 1.52 | 1.03 | 0.69 | 1.0 | 0.00 |
| SdD5D | 9.97 | 8.26 | 1.67 | 0.87 | 0.6 | 15.95 | 9.49 | 1.47 | 1.04 | 0.67 | 1.0 | 0.29 |
| SdD5D | 11.74 | 7.90 | 2.31 | 1.41 | 0.8 | 15.54 | 7.60 | 1.52 | 1.26 | 0.74 | 1.0 | 0.00 |
| SdD5D | 10.14 | 6.60 | 3.52 | 2.45 | 0.6 | 17.21 | 7.45 | 3.80 | 3.79 | 0.25 | 1.0 | 0.07 |
| SdD5D | 14.47 | 8.99 | 1.87 | 1.34 | 0.6 | 20.24 | 8.57 | 1.33 | 1.42 | 0.76 | 0.9 | |
| SdD5D | 7.12 | 5.77 | 1.75 | 1.33 | 0.6 | 10.82 | 5.21 | 1.24 | 1.28 | 0.91 | 0.9 | 0.12 |
| SdD5D | 11.56 | 8.11 | 1.76 | 1.55 | 0.6 | 16.70 | 7.63 | 1.05 | 1.41 | 0.90 | 0.8 | 0.00 |
| SdD5D | 11.29 | 8.28 | 2.70 | 1.12 | 0.3 | 19.81 | 10.54 | 3.05 | 2.00 | 0.14 | 0.7 | 0.22 |
| SdD5D | 12.68 | 8.86 | 1.22 | 1.27 | 0.5 | 14.48 | 7.39 | 0.81 | 1.19 | 0.79 | 0.7 | 0.25 |
| SdD5D | 9.49 | 7.11 | 2.05 | 1.39 | 0.3 | 17.21 | 9.63 | 3.14 | 2.50 | 0.01 | 0.6 | 0.00 |
| SdD5D | 13.22 | 9.18 | 1.54 | 0.97 | 0.5 | 18.75 | 8.41 | 0.88 | 0.84 | 0.41 | 0.6 | 0.00 |
| SdD5D | 12.13 | 9.46 | 2.06 | 1.28 | 0.2 | 19.45 | 11.20 | 2.24 | 2.01 | 0.12 | 0.6 | 0.00 |
| SdD5D | 8.53 | 7.40 | 1.49 | 0.62 | 0.4 | 13.52 | 7.75 | 1.03 | 0.69 | 0.47 | 0.5 | |
| SdD5D | 7.82 | 9.32 | 0.50 | 0.32 | 0.2 | 14.56 | 9.62 | 0.45 | 0.37 | 0.00 | 0.4 | 0.19 |
| SdD5D | 13.65 | 12.00 | 0.44 | 0.28 | 0.2 | 22.20 | 14.32 | 0.37 | 0.35 | 0.18 | 0.3 | |
| SdD5D | 32.50 | 3.67 | 1.65 | 6.99 | 0.3 | 11.88 | 2.60 | 1.07 | 2.44 | 0.05 | 0.2 | |
| SdD5D | 14.53 | 10.71 | 3.32 | 1.17 | 0.0 | 21.25 | 9.46 | 3.16 | 1.69 | 0.02 | 0.0 | 0.30 |
| SdD5D | 15.47 | 13.31 | 0.00 | 0.07 | 0.0 | 25.00 | 13.74 | 0.00 | 0.00 | 0.00 | 0.0 | 0.12 |
| IgD5D | 10.26 | 7.52 | 0.64 | 1.67 | 3.0 | 18.27 | 8.04 | 1.31 | 3.16 | 0.00 | 3.1 | |
| IgD5D | 11.88 | 8.04 | 0.85 | 1.83 | 3.7 | 17.40 | 6.53 | 1.20 | 2.76 | 0.00 | 2.9 | |
| IgD5D | 12.35 | 9.90 | 0.39 | 1.14 | 3.0 | 19.15 | 9.90 | 0.76 | 1.70 | 0.00 | 2.7 | |
| IgD5D | 10.76 | 6.76 | 0.61 | 2.43 | 2.4 | 17.37 | 7.17 | 1.27 | 3.88 | 0.00 | 2.6 | |
| IgD5D | 9.23 | 8.57 | 0.50 | 0.74 | 2.5 | 17.26 | 10.46 | 1.02 | 1.29 | 0.00 | 2.6 | |

TABLE 4-continued

Delta 5 desaturase activity of *Hemiselmis* spp. HvD5D and HrD5D in soy
(Fatty acids 18:3 and greater).

| Element | LA | GLA | DGLA | EDA | AA | ALA | SDA | ETA | EtrA | JA | EPA | DPA |
|---|---|---|---|---|---|---|---|---|---|---|---|---|
| IgD5D | 12.04 | 9.80 | 0.25 | 1.05 | 2.8 | 21.77 | 9.66 | 0.86 | 1.98 | 0.00 | 2.6 | |
| IgD5D | 14.29 | 9.96 | 0.47 | 1.22 | 2.9 | 20.20 | 8.03 | 0.83 | 1.85 | 0.00 | 2.3 | |
| IgD5D | 5.01 | 3.35 | 1.15 | 1.51 | 2.0 | 9.62 | 4.62 | 2.63 | 2.52 | 0.00 | 2.3 | |
| IgD5D | 14.52 | 9.96 | 0.67 | 1.18 | 2.7 | 18.26 | 8.32 | 0.83 | 1.52 | 0.00 | 2.2 | |
| IgD5D | 14.17 | 8.57 | 0.48 | 1.89 | 2.4 | 20.34 | 8.34 | 0.66 | 2.30 | 0.00 | 2.2 | |
| IgD5D | 16.82 | 9.91 | 0.66 | 1.16 | 2.5 | 18.54 | 7.47 | 0.74 | 1.33 | 0.00 | 1.8 | |
| IgD5D | 16.22 | 11.17 | 0.37 | 1.07 | 2.4 | 19.85 | 9.13 | 0.41 | 1.40 | 0.00 | 1.7 | |
| IgD5D | 11.72 | 10.05 | 0.39 | 0.67 | 1.8 | 20.12 | 10.56 | 0.75 | 1.20 | 0.00 | 1.7 | |
| IgD5D | 10.83 | 7.99 | 2.48 | 1.56 | 0.4 | 20.94 | 10.26 | 3.79 | 2.90 | 0.02 | 0.3 | |
| IgD5D | 12.64 | 6.44 | 2.45 | 2.32 | 0.3 | 19.38 | 8.14 | 4.14 | 3.80 | 0.00 | 0.2 | |
| IgD5D | 15.94 | 4.43 | 2.51 | 4.11 | 0.2 | 17.48 | 5.61 | 4.56 | 5.22 | 0.00 | 0.1 | |
| IgD5D | 17.93 | 3.31 | 0.72 | 3.22 | 0.0 | 8.02 | 5.05 | 0.69 | 0.99 | 0.00 | 0.0 | |
| IgD5D | 15.45 | 12.73 | 0.00 | 0.01 | 0.0 | 21.43 | 13.30 | 0.00 | 0.00 | 0.00 | 0.0 | |

The *H. virescens* and the *H. rufescens* Δ5 desaturases both produced on average approximately 3-fold more EPA than AA indicating an omega-3 substrate preference. The 18:2 D5,9 and 18:2 D6,9 fatty acids were at or below 0.5%. In contrast, the *Isochrysis galbana* Δ5 desaturase produced slightly higher AA levels in comparison to EPA levels, indicating a slight preference for omega-6 fatty acids. The *Saproligna diclina* Δ5 desaturase produced 2.5% 18:2 D5,9 on average while producing less than 1% EPA on average.

Example 4

Expression of the *Hemiselmis* Spp. Δ5-Desaturases in Corn

In many monocotyledonous plants such as corn (*Zea mays*) the majority of the oil is accumulated in the germ. Engineering polyunsaturated fatty acid biosynthesis in these plants can therefore efficiently be achieved by expressing the Δ5 desaturase, as well as the complimentary desaturases and elongases (the background enzymes) under the control of germ-specific promoters such as the oleosin promoter, the glob promoter, or the *Hordeum vulgare* PER1 promoter. In addition, introns such as the HSP70 intron, or the rice actin intron are frequently added in the 5'-UTR sequence in order to enhance gene expression in monocotyledonous plants. Furthermore, the Kozak sequence may be slightly modified to reflect preferences for expression in monocotyledonous plants. All other aspects of the plant background and the expression cassette of interest remain equivalent to Example 3.

Transformed corn explants containing constructs as described above are obtained via *Agrobacterium tumefaciens*-mediated transformation. Plants are regenerated from transformed tissue. The greenhouse-grown plants are then analyzed for oil composition.

All of the compositions and methods disclosed and claimed according to the current invention can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit or scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background, or teach methodology, techniques, and/or compositions employed herein.

U.S. Pat. No. 4,518,584; U.S. Pat. No. 4,737,462; U.S. Pat. No. 4,810,648; U.S. Pat. No. 4,957,748; U.S. Pat. No. 5,094,945; U.S. Pat. No. 5,100,679; U.S. Pat. No. 5,196,525; U.S. Pat. No. 5,219,596; U.S. Pat. No. 5,290,924; U.S. Pat. No. 5,322,783; U.S. Pat. No. 5,359,142; U.S. Pat. No. 5,424,398; U.S. Pat. No. 5,500,365; U.S. Pat. No. 5,530,196; U.S. Pat. No. 5,424,412; U.S. Pat. No. 5,538,880; U.S. Pat. No. 5,550,318; U.S. Pat. No. 5,563,055; U.S. Pat. No. 5,610,042; U.S. Pat. No. 5,627,061; U.S. Pat. No. 5,633,435; U.S. Pat. No. 5,641,876; U.S. Pat. No. 5,936,069; U.S. Pat. No. 6,005,076; U.S. Pat. No. 6,040,497; U.S. Pat. No. 6,051,753; U.S. Pat. No. 6,146,669; U.S. Pat. No. 6,156,227; U.S. Pat. No. 6,265,638; U.S. Pat. No. 6,319,698; U.S. Pat. No. 6,433,252; U.S. Pat. No. 6,451,567.

U.S. Patent Application Publication 20030093828; U.S. Patent Application Publication 20030229918; US Patent Application Publication 20070271632.

Barany et al., *Int. J. Peptide Protein Res.*, 30:705-739, 1987.
Bauer et al., *Gene*, 37:73, 1985.
Belanger and Kriz, *Genetics*, 129:863-872, 1991.
Bevan et al., *Nucleic Acids Res.*, 11:369-385, 1983.
Bodanszky, In: Principles of Peptide Synthesis, Springer-Verlag, Heidelberg, 1984.
Bustos et al., *Plant Cell*, 1:839-853, 1989.
Callis et al., *Genes Dev.*, 1:1183-1200, 1987.
Chen et al., *Proc. Natl. Acad. Sci. USA*, 83:8560-8564, 1986.
Chu et al., *Scientia Sinica*, 18:659, 1975.
DeBlock et al., *EMBO J.*, 6:2513-2519, 1987.
Ebert et al., *Proc. Natl. Acad. Sci. USA*, 84:5745-5749, 1987.
Freitag and Selker, *Curr Opin Genet Dev.* 15:191-9, 2005.
Gallie et al., *The Plant Cell*, 1:301, 1999.
Haymes et al., (Nucleic Acid Hybridization, A Practical Approach, IRL Press, Washington, D.C., 1985.
Hudspeth et al., *Plant Mol. Biol.*, 12:579, 1989.
Ingelbrecht et al., *Plant Cell*, 1:671-680, 1989.
Joshi, *Nucleic Acids Res*, 15:6643, 1987.
Kridl et al., *Seed Sci. Res.*, 1:209-219, 1991.

Lopes et al., *Mol. Gen. Genet.*, 247:603-613, 1995.
Maniatis et al., *Molecular Cloning, A Laboratory Manual*, Cold Spring Harbor Press, Cold Spring Harbor, N.Y., 1989.
Maundrell, *J. Biol. Chem.*, 265:10857-10864, 1990.
McElroy et al., *Mol Gen Genet.* 231:150-160, 1991.
Merrifield, *J. Am. Chem. Soc.*, 85:2149-2154, 1963.
Misawa et al., *Plant J.*, 6:481-489, 1994.
Murashige and Skoog, *Physiol. Plant*, 15:473-497, 1962.
Napier et al., *Biochem. J.*, 328, 717-720, 1997.
Napier et al., *Prostaglandins Leukot. Essent. Fatty Acids*, 68:135-143, 2003. PCT Publications WO 02/050295; WO 95/06128; WO 96/33155
Prem Das et al., *NAR*, 19:3325-3330, 1991.
Recombinant DNA Part D, *Methods in Enzymology*, 153:1-622, Wu and Grossman (Eds.), Academic Press, 1987.
Sambrook et al., *In: Molecular cloning*, Cold Spring Harbor Laboratory Press, Cold Spring Harbor, N.Y., 2001.
Sathasiivan et al., *Nucl. Acids Res.*, 18:2188-2193, 1990.
Sperling and Heinz, *Eur. J. Lipid Sci. Technol.*, 103:158-180, 2001.
Stacey et al., *Plant Mol. Biol.*, 31:1205-1216, 1996.
Turner and Foster, *Mol. Biotechnol.*, 3:225-36, 1995.
Vasil et al., *Plant Physiol.*, 91:1575-1579, 1989.
Walder et al. *Gene*, 42:133, 1986.
Wohlleben et al., *Gene*, 70:25-37, 1988.

The invention claimed is:

1. A polynucleotide molecule comprising a nucleic acid sequence selected from the group consisting of:
   a) a nucleic acid sequence encoding the polypeptide sequence of SEQ ID NO:2 or SEQ ID NO:4;
   b) a nucleic acid sequence of SEQ ID NO:1 or SEQ ID NO:3;
   c) a nucleic acid sequence that hybridizes to SEQ ID NO:1 or SEQ ID NO:3 or a complement thereof, under conditions of 5×SSC, 50% formamide and 42° C. and encodes a polypeptide having desaturase activity that desaturates a fatty acid molecule at carbon 5; and
   d) a nucleic acid sequence encoding a polypeptide with at least 75% sequence identity to a polypeptide sequence of SEQ ID NO:2 or SEQ ID NO:4 having desaturase activity that desaturates a fatty acid molecule at carbon 5, wherein the polynucleotide molecule is operable linked to a heterologous promoter.

2. The polynucleotide molecule of claim 1, comprising a nucleic acid sequence encoding the polypeptide sequence of SEQ ID NO:2 or SEQ ID NO:4.

3. The polynucleotide molecule of claim 1, comprising a nucleic acid sequence of SEQ ID NO:1 or SEQ ID NO:3.

4. The polynucleotide molecule of claim 1, comprising a nucleic acid sequence that hybridizes to SEQ ID NO:1 or SEQ ID NO:3, under conditions of 5×SSC, 50% formamide and 42° C. and encodes a polypeptide having desaturase activity that desaturates a fatty acid molecule at carbon 5, or the full complement thereof.

5. The polynucleotide molecule of claim 1, comprising a nucleic acid sequence encoding a polypeptide with at least 75% sequence identity to a polypeptide sequence of SEQ ID NO:2 or SEQ ID NO:4 having desaturase activity that desaturates a fatty acid molecule at carbon 5.

6. The polynucleotide molecule of claim 1, comprising a nucleic acid sequence encoding a polypeptide having at least one of the amino acid motifs selected from the group consisting of: SEQ ID NO: 15, SEQ ID NO: 16, SEQ ID NO:17, SEQ ID NO: 18, SEQ ID NO: 19, SEQ ID NO: 20, SEQ ID NO: 21, SEQ ID NO:22, and SEQ ID NO: 23.

7. The polynucleotide molecule of claim 1, further comprising at least one additional polynucleotide sequence encoding fatty acid elongase or desaturase.

8. The polynucleotide molecule of claim 1, wherein the heterologous promoter is a seed-enhanced promoter.

9. A host cell transformed with the polynucleotide molecule of claim 1.

10. The host cell of claim 9, wherein the host cell is a plant cell, a fungal cell or bacterial cell.

11. The host cell of claim 9, wherein the host cell exhibits altered fatty acid biosynthesis relative to a cell of the same genotype as said host cell but lacking said polynucleotide molecule.

12. The host cell of claim 9, wherein the cell has inherited said polynucleotide molecule from a progenitor of the cell.

13. A transgenic plant or plant part transformed with the polynucleotide molecule of claim 1.

14. The transgenic plant or plant part of claim 13 wherein the plant is selected from the group consisting of canola, Brassica campestris, oilseed rape, rapeseed, soybean, crambe, mustard, castor bean, peanut, sesame, cottonseed, linseed, safflower, oil palm, flax, sunflower, corn, rice, barley, millet, rye, wheat, oat, alfalfa and sorghum.

15. The transgenic plant or plant part of claim 13, further comprising at least one additional polynucleotide encoding a fatty acid desaturase or elongase.

16. The transgenic plant or plant part of claim 15, further comprising a polynucleotide encoding a Δ6 desaturase, a Δ6 elongase, a Δ18 elongase, a Δ15 desaturase, a Δ9 elongase, a Δ8 desaturase, a Δ17 desaturase, a Δ4 desaturase or a C20 elongase.

17. A progeny plant of a transgenic plant comprising the polynucleotide molecule of claim 1, wherein the progeny plant comprises said polynucleotide molecule.

18. A seed of a transgenic plant comprising the polynucleotide molecule of claim 1, wherein the seed comprises said polynucleotide molecule.

19. A commercial product obtained from a plant comprising the polynucleotide molecule of claim 1, wherein the product comprises said polynucleotide molecule.

20. The commercial product of claim 19, wherein the commercial product is a food or feed.

21. The commercial product of claim 20, wherein the food or feed is oil, silage, meal, grain, starch, flour or protein.

22. The commercial product of claim 19, wherein the commercial product comprises EPA, ARA and/or DHA.

23. A method of producing a food or feed composition, comprising the steps of:
   (a) obtaining the transgenic plant or plant part according to claim 13; and
   (b) producing said food or feed composition.

24. The method of claim 23, wherein the food or feed is oil, silage, meal, grain, starch, flour or protein.

* * * * *